(12) United States Patent
Miyata et al.

(10) Patent No.: US 7,972,788 B2
(45) Date of Patent: Jul. 5, 2011

(54) SKIN AGING MARKER AND TECHNIQUE FOR USE THEREOF

(75) Inventors: Satoshi Miyata, Yokohama (JP); Kaoru Miyazaki, Fujisawa (JP); Chie Yasuda, Machida (JP); Akihiro Iwamatsu, Yokohama (JP)

(73) Assignees: Fancl Corporation, Yokohama-shi (JP); Yokohama City University, Yokohama-shi (JP); Kihara Memorial Yokohama Foundation for the Advancement of Life Sciences, Yokohama-shi (JP); Kirin Holdings Kabushiki Kaisha, Tokyo (JP)

( * ) Notice: Subject to any disclaimer, the term of this patent is extended or adjusted under 35 U.S.C. 154(b) by 453 days.

(21) Appl. No.: 12/064,602

(22) PCT Filed: Aug. 22, 2006

(86) PCT No.: PCT/JP2006/316407
§ 371 (c)(1),
(2), (4) Date: Feb. 22, 2008

(87) PCT Pub. No.: WO2007/023808
PCT Pub. Date: Mar. 1, 2007

(65) Prior Publication Data
US 2009/0305242 A1    Dec. 10, 2009

(30) Foreign Application Priority Data

Aug. 23, 2005   (JP) ................................ 2005-240820

(51) Int. Cl.
| | | |
|---|---|---|
| C12Q 1/68 | (2006.01) | |
| G01N 33/53 | (2006.01) | |
| C07K 1/00 | (2006.01) | |
| C07K 14/00 | (2006.01) | |
| C07K 17/00 | (2006.01) | |
| A61K 38/17 | (2006.01) | |
| C08H 1/06 | (2006.01) | |

(52) U.S. Cl. .............. 435/6; 435/7.1; 530/350; 530/357
(58) Field of Classification Search .................. None
See application file for complete search history.

(56) References Cited

FOREIGN PATENT DOCUMENTS

| | | |
|---|---|---|
| JP | 2001-212087 | 8/2001 |
| JP | 2002-511240 | 4/2002 |
| JP | 2002-330943 | 11/2002 |
| JP | 2002-360544 | 12/2002 |
| WO | WO 02/074911 A2 | 9/2002 |
| WO | WO 2004/005462 A2 | 1/2004 |

OTHER PUBLICATIONS kyng, K.J. et al., PNAS USA, vol. 100, pp. 12259-12264, 2003.*
Sugarman, B. et al., Life Sciences, vol. 26, pp. 915-920 (1980).*
Hildebran, J.N. et al., In Vitro, vol. 19, pp. 307-314 (1983).*
G.P. Dimri, et al., "A biomarker that identifies senescene human cells in culture and in aging skin in vivo," Proc. Natl. Acad. Sci. USA, vol. 92, pp. 9363-9367, Sep. 1995.
S. Tsuzuki, "Molecular Nutritional Studies on Serine Proteases and Their Inhibitors That Regulate Cell Turnover of Intestinal Mucosal Epithelium," J. Jpn Soc. Nutr. Food Sci., vol. 57, pp. 277-282, 2004.
Alice Y.-C, et al., "Heat shock induction of HSP 89 is regulated in cellular aging," Biochem. Biophy. Res. Commun., vol. 162, No. 3, pp. 1302-1310, Aug. 15, 1989.
J. Krishnamurthy, et al., "Ink4a/Arf expression is a biomarker of aging," The Journal of Clinical Investigation, vol. 114, No. 9, Nov. 2004.
M. R. Khorramizadeh, et al., "Aging differentially modulates the expression of collagen and collagenase in dermal fibroblasts," Molecular and Cellular Biochemistry, vol. 194, pp. 99-108, 1999.
B. Le Varlet, et al.,"Age-Related Functional and Structural Changes in Human Dermo-Epidermal Junction Components," Dermo-Epidermal Junction and Aging, vol. 3, No. 2, pp. 172-179, Aug. 1998.
Gail Jenkins, "Molecular mechanisms of skin ageing," Mechanisms of Ageing and Development, vol. 123, pp. 801-810, 2002.
Isabelle Petropoulos, et al., "Increase of Oxidatively Modified Protein Is Associated With a Decrease of Proteasome Activity and Content in Aging Epidermal Cells," Journal of Geromology: Biological Sciences, vol. 55A, No. 5, pp. B220-B227, 2000.
T. Tezuka, et al., "Terminal Differentiation of Facial Epidermis of the Aged: Immunohistochemical Studies," Clinical and Laboratory Investigations, Dermatology, vol. 188, pp. 21-24, 1994.
B.J. Nickoloff, et al., "Tumor Suppressor Maspin Is Up-Regulated during Keratinocyte Senescence, Exerting a Paracrine Antiangiogenic Activity," Cancer Research, vol. 64, pp. 2956-2961, May 1, 2004.
J-H Baek, et al., "Common genes responsible for differentiation and senescence of human mucosal and epidermal keratinocytes," Int. J. Mol. Med, vol. 12, pp. 319-325, 2003.
P. Gromov, et al., "Protein Profiling of Human Epidermis from the Elderly Reveals Up-Regulation of a Signature of Interferon-γ-induced Polypeptides That Includes Managanese-superoxide Dismutase and the p85β Subunit of Phosphatidylinositol 3-Kinase," Mol. & Cell. Proteomics, vol. 2, No. 2, pp. 70-84, 2003. M.D. West, et al., "Altered Expression of Plasminogen Activator and Plasminogen Activator Inhibitor During Cellular Sensescene," Experimental Gerontology, vol. 31, No. 1/2, pp. 175-193, 1996.
S. Murano, et al., "Diverse Gene Sequences Are Overexpressed in Wwrner Syndrome Fibroblasts Undergoing Premature Replicative Senescence," Molecular and Cellular Biology, vol. 11, No. 8, pp. 3905-3914, 1991.

(Continued)

*Primary Examiner* — Teresa E Strzelecka
(74) *Attorney, Agent, or Firm* — Knobbe Martens Olson & Bear LLP

(57) ABSTRACT

It is an object of the present invention to find substances that can be used as skin aging markers, and the present invention provides a method for determining the degree of skin aging, including measurement of expression of secretory proteins and/or intracellular proteins and/or their genes in skin cells and/or skin tissues, wherein the secretory proteins and/or intracellular proteins change their expression with aging of skin. The present invention also provides a kit for determining the degree of skin aging and a method for identifying substances effective in the prevention of skin aging.

5 Claims, 23 Drawing Sheets

OTHER PUBLICATIONS

S. Wang, et al., "Characterization of IGFBP-3, PAI-I and SPARC mRNA expression in senescent fibroblasts," Mechanism of Ageing and Development, vol. 92, pp. 121-132, 1996.

A. Gutsmann-Conrad, et al., "The Expression of Heat Shock Protein 70 Decrease with Cellular Senescence in vitro and in Cells Derived from Young and Old Human Subjects," Experimental Cell Research, vol. 241, pp. 404-413, 1998.

H-S Yang, et al., "Increased Ezrin Expression and Activation by CDK5 Coincident with Acquisition of the Senescent Phenotype," Molecular Cell, vol. 11, pp. 1163-1176, May 2003.

J.S Ahn, et al., "Aging-associated increase of gelsolin for apoptosis resistance," Biochem. Biophys. Res. Commun., vol. 312, pp. 1335-1341, 2003.

M. W-F. Chang, et al., "Comparison of early passage, senescent and hTERT immortalized endothelial cells, " Experimental Cell Research., vol. 309, pp. 121-136, Jun. 2005.

M. Martine, et al., "From Newborn to Adult: Phenotypic and Functional Properties of Skin Equivalent and Human Skin as a Function of Donor Age," J. Cell. Physio., vol. 171, No. 2, pp. 179-189, 1997.

S. Lyle, et al., "Cytokeratin 15(K15) as an epithelial stem cell marker: Implication for aging and carcinogenesis," J. Invest. Dermatol., vol. 112, No. 4, pp. 623, 1999.

N.A. Saunders, et al., "Regulation of Proliferation: Specific and Differentiation-Specific Genes During Senescene of Human Epidermal Keratinocytes and Mammary Epithelial Cells," Biochem. Biophys. Res. Commun., vol. 197, No. 1, pp. 46-54, 1993.

E. Olsen, et al., "Identification of proteins that are abnormally regulated in differentiated cultured human keratinocytes," Electrophoresis, vol. 16, pp. 2241-2248, 1995.

Goos N.P. Van Muijen, et al., "Differentiation-Related Changes of Cytokeratin Expression in Cultured Keratinocytes and in Fetal, Newborn, and Adult Epidermis," Experimental Cell Research., vol. 171, pp. 331-345, 1987.

T. Kishi, et al., "Development of an Immunofluorometric Assay and Quatification of Human Kallikrein 7 in Tissue Extracts and Biological Fluids," Clinical Chemistry, vol. 50, No. 4, pp. 709-716, 2004.

L. J. Robinson, et al., "Proteomic Analysis of the Genetic Premature Aging Disease Hutchinson Gilford Progeria Syndrome Reveals Differential Protein Expression and Glycosylation," J. Proteme Research, vol. 2, pp. 556-557, 2003.

Tomonaga Yasuda, "Changes in Secretory Proteins with Aging of Epidermal Cells," Kihara Memorial Yokohama Foundation for the Advancement of Life Sciences, pp. 37-39, 2002.

N. Komatsu, et al., "Quantification of Human Tissue Kallikreins in the Stratum Corneum: Dependence on Age and Gender," J. Invest. Dermatol., vol. 125, No. 6, pp. 1182-1189, Dec. 2005.

B.W. Darbro, et al., "Co-Regulation of $p161^{INK4a}$ and Migratory Genes in Culture Conditions that Lead to Premature Senescence in Human Keratinocytes," J. Invest. Dermatol., vol. 125, No. 3, pp. 499-509, Sep. 2005.

* cited by examiner

[Fig. 1]
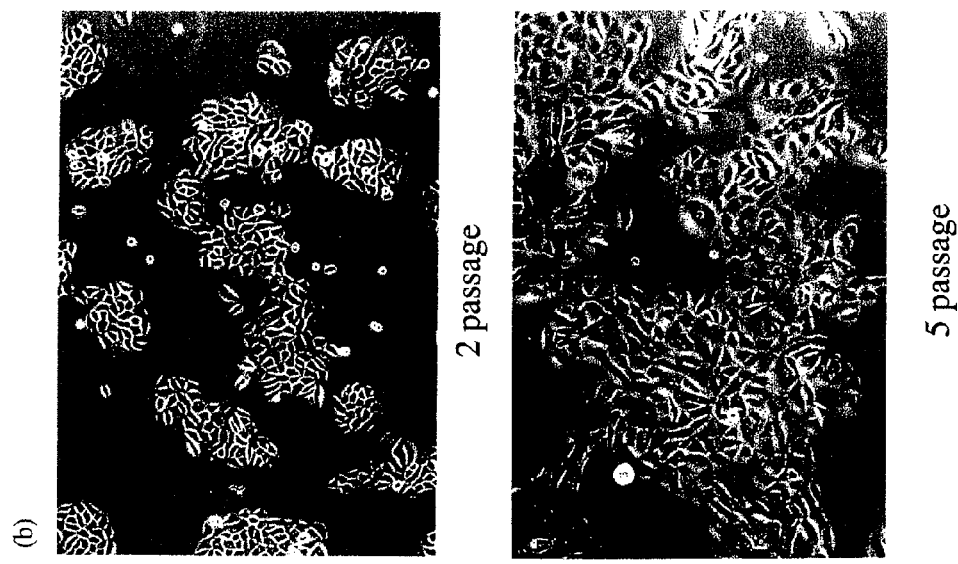
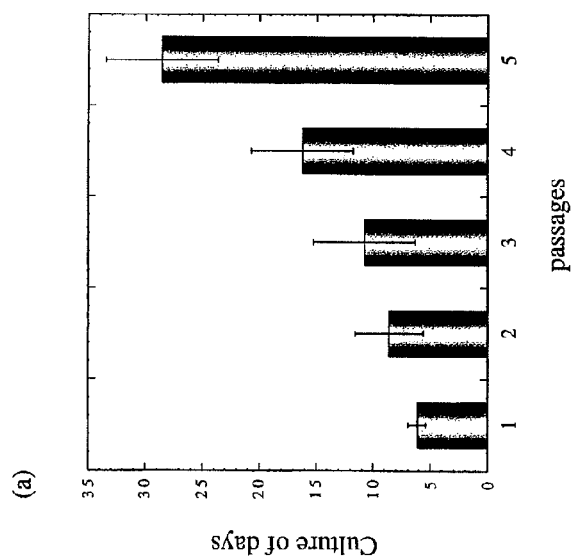

[Fig. 2]
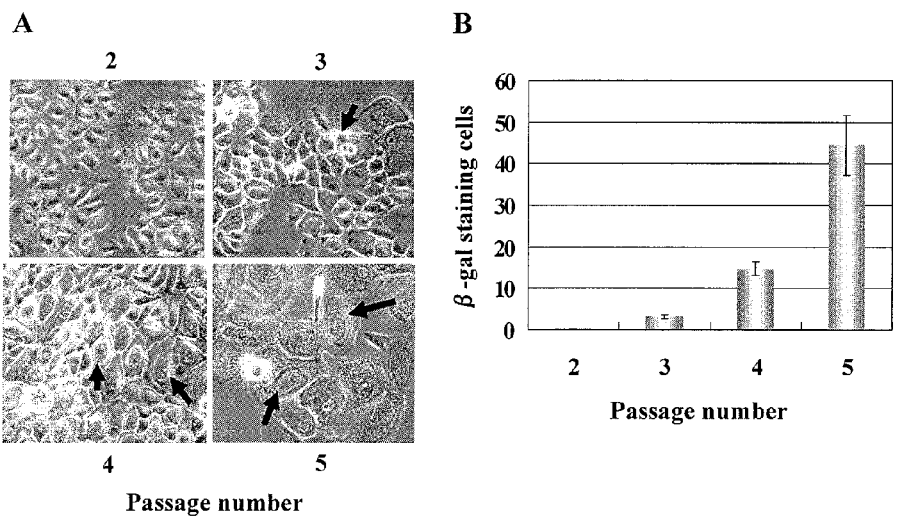

5 passage

Fig. 3(c)

| | |
|---:|---|
| 8 | Fatty acid binding protein 5 |
| 9 | Profilin-1 |
| 12, 22, 221 | Cystatin M precursor |
| 18 | Phosphoglycerate mutase 1 |
| 21, 23, 219, 220, 222 | Beta-2 microglobulin |
| 24 | Fatty acid binding protein 5 |
| 31 | Actin related protein 2/3 complex subunit 5 |
| 32 | Proteasome subunit beta 5 |
| 33 | Peroxiredxin 1 |
| 35 | Proteasome subunit beta 1 |
| 36 | Proteasome subunit alpha 7 |
| 39 | Mitochondrial maltate dehydrogenase |
| 42, 59 | Tim |
| 51 | Manganese superoxide dismutase |
| 62 | Proteasome subunit beta 3 |
| 64, 68 | HSP27 |
| 67 | Proteasome beta7 subunit proprotein |
| 71 | Glutathion transferase |
| 80 | Proteasome subunit alpha 6 |
| 86 | Purine nucleoside phosphorylase |
| 90 | Dienoyl-CoA isomerase |
| 94 | L-lactate dehydrogenase B |
| 98 | Hypothetical protein |
| 100 | Tubulin, beta 5 |
| 105 | Maspin precursor |
| 122 | SCCA1 |
| 125, 128, 129, 241 | Annexin 2 |
| 136 | Annexin 1 |
| 140 | Cytosolic maltate dehydrogenase |
| 143 | Phosphglycerate kinase 1 |
| 145 | Fructose-bisphosphate aldolase A |
| 152 | Adenosyl homocysteinase |
| 160 | Cytosolic nonspecific dipeptidase |
| 161 | Actin-related protein 3 |
| 163 | Glutathione synthetase |
| 168 | Transketolase |
| 172 | Pyruvate kinase, M1 isozyme |

Fig. 3(d)

| | |
|---|---|
| 176, 178 | UTP-glucose-1-phosphate uridyl transferase 2 |
| 177 | Adenylyl cyclase-associated protein 1 |
| 183 | Elongation factor 2 |
| 184 | Moesin |
| 185 | Ezrin |
| 186 | Ubiquitin carboxyl-terminal hydrolase 14 |
| 187 | Keratin 9 |
| 188 | Heat shock cognate 71 KDa protein |
| 189 | Gelsolin |
| 191 | Tubulin, alpha 6 |
| 193 | Acylamino-acid releasing enzyme |
| 195 | Transitional endplasmic reticulum ATPase |
| 196 | Actin, alpha 1 |
| 197 | Major vault protein |
| 199 | Vinculin isoform VCL |
| 200, 201 | Keratin 1 |
| 204 | Leukotriene A4 hydrolase |
| 206, 207 | PAI-1 |
| 208 | Enolase-1 |
| 209 | Asparatate transaminase |
| 210, 211 | SCCA1 |
| 212 | Phosphoglycerate mutase 1 |
| 213 | Peroxiredoxin 6 |
| 214 | IPP isomerase 1 |
| 216, 215 | HSP27 |
| 217 | ER-localized type I transmembrane adaptor precursor |
| 218 | Glutathion S-transferase Pi |
| 223 | Integrin-linked kinase 1 |
| 226 | Kallikrein 7 |
| 227 | RhoGDP dissociation inhibitor(GDI)alpha |
| 228 | Thrombospondin 1 |
| 230 | Cystatin A |
| 235 | HSP70 |
| 239 | 60S acidic ribo-somal protein P0 |
| 240 | Rho GDP-dissociation inhibitor 1 |
| 242 | Caspase 14 precursor |

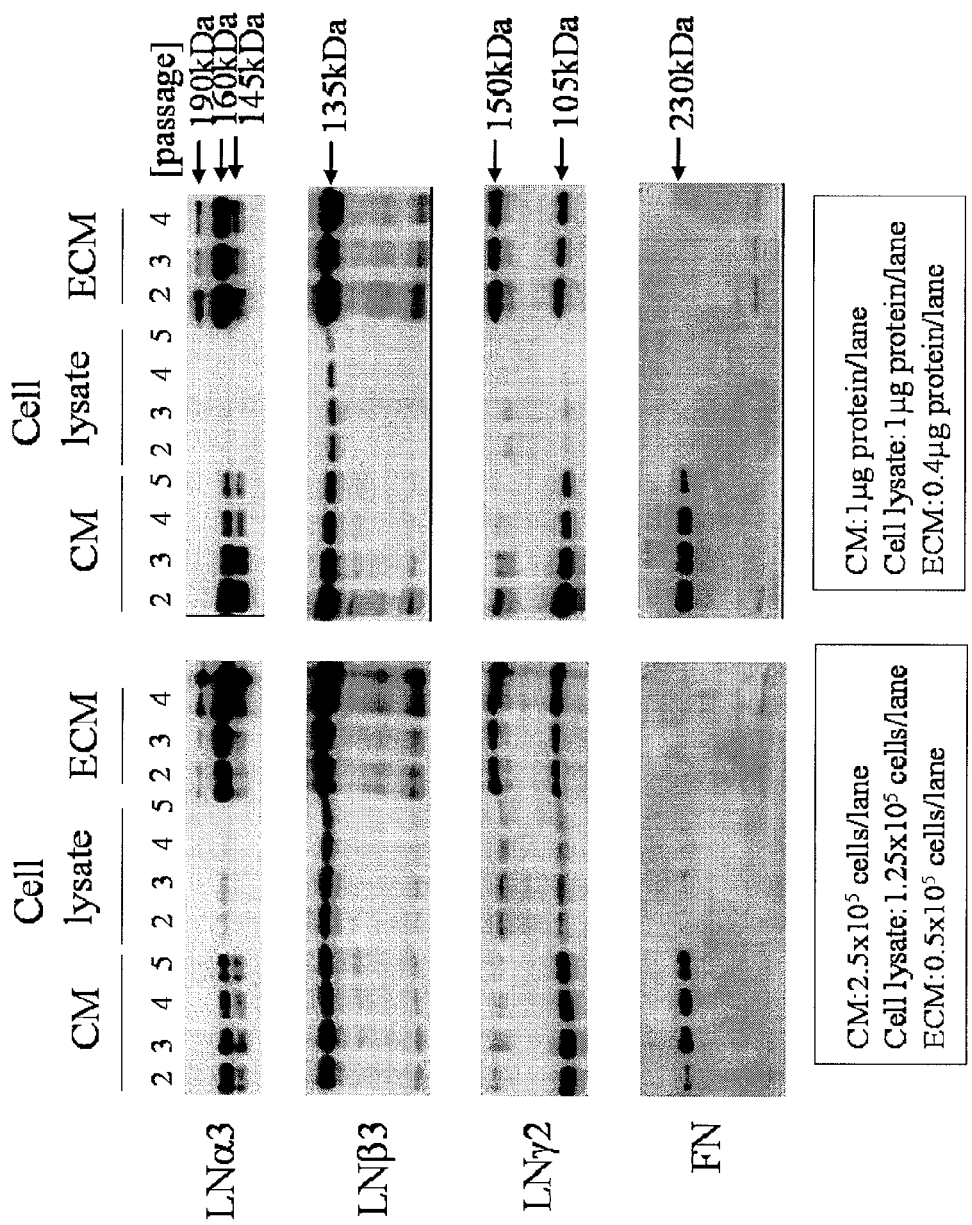
[Fig. 4]

[Fig. 5(a)]
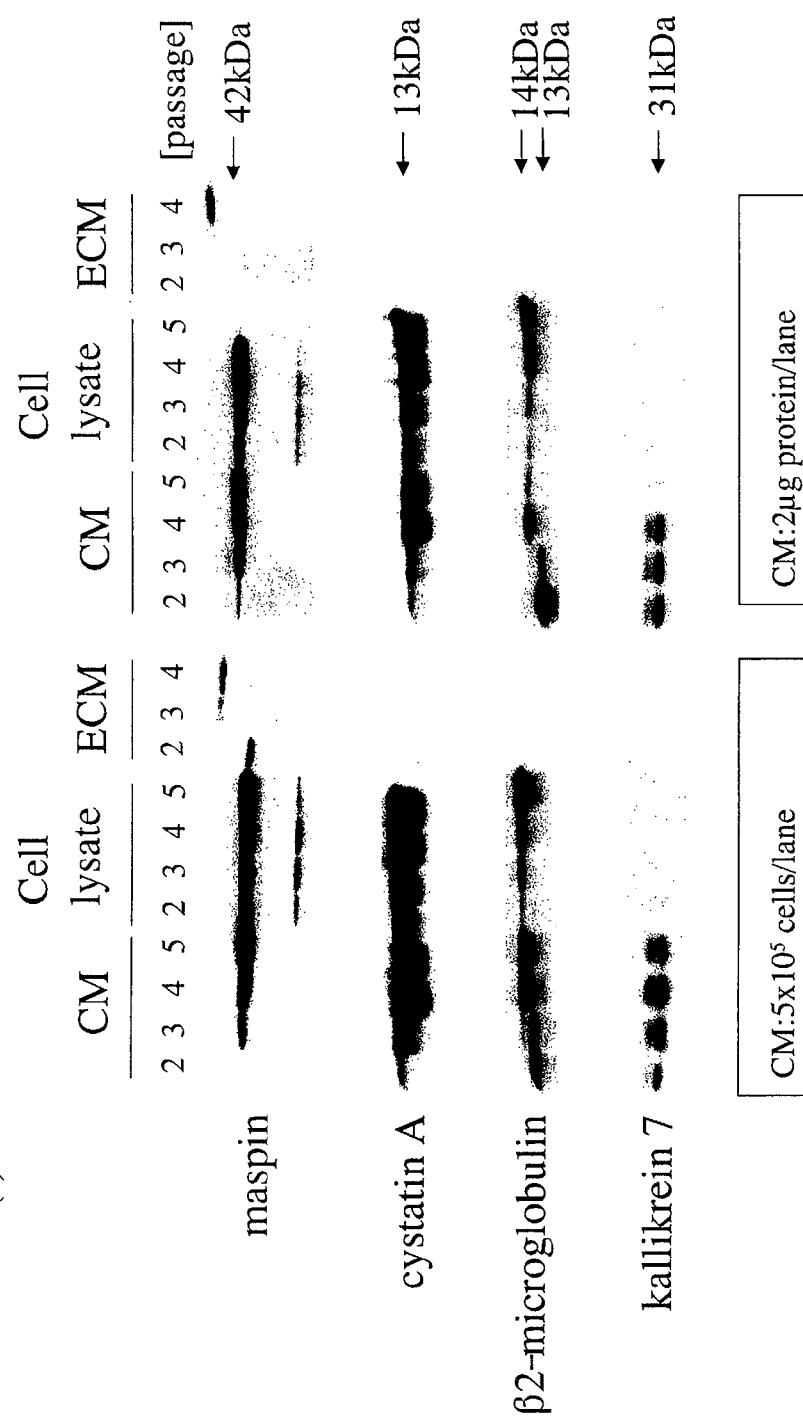

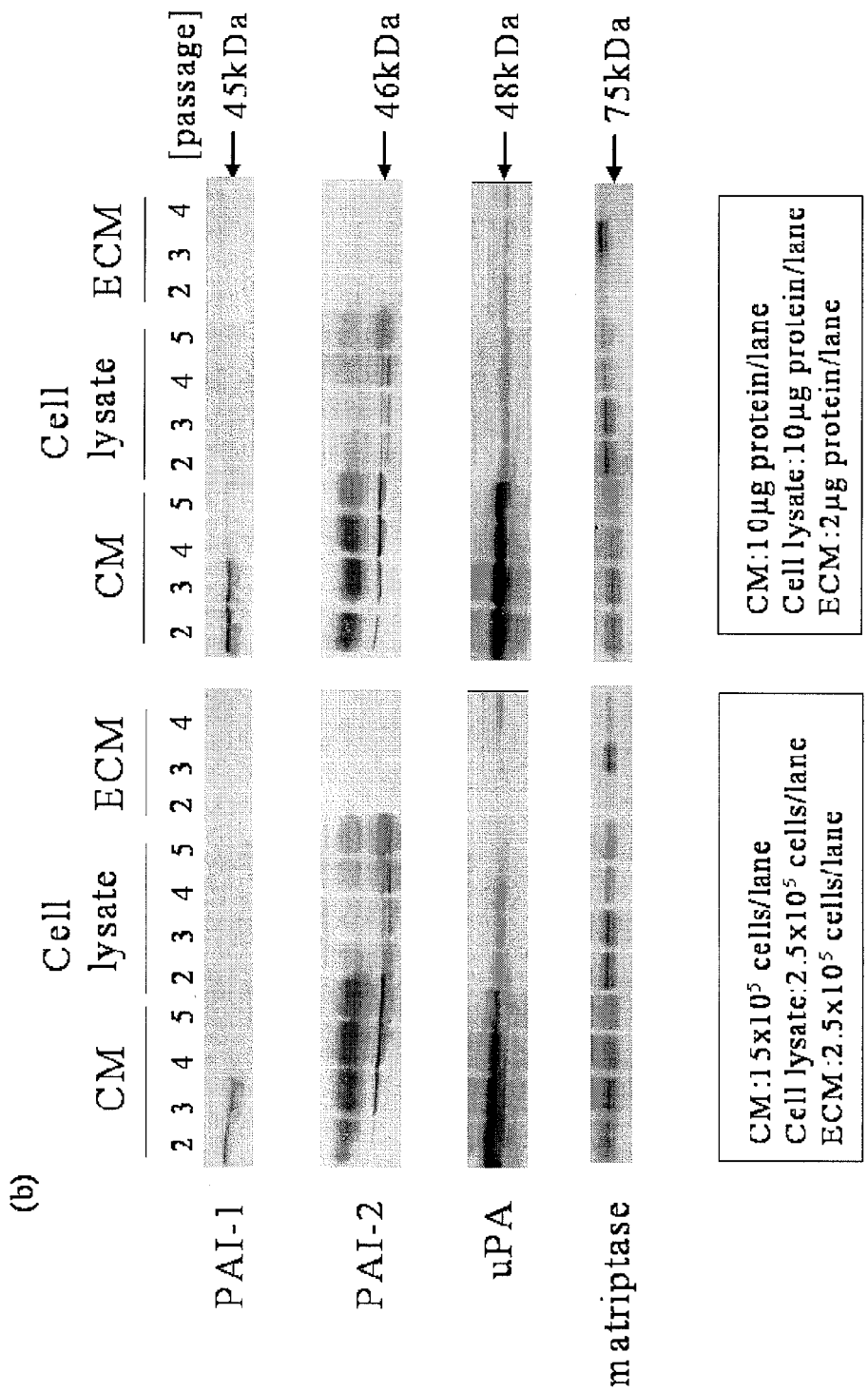

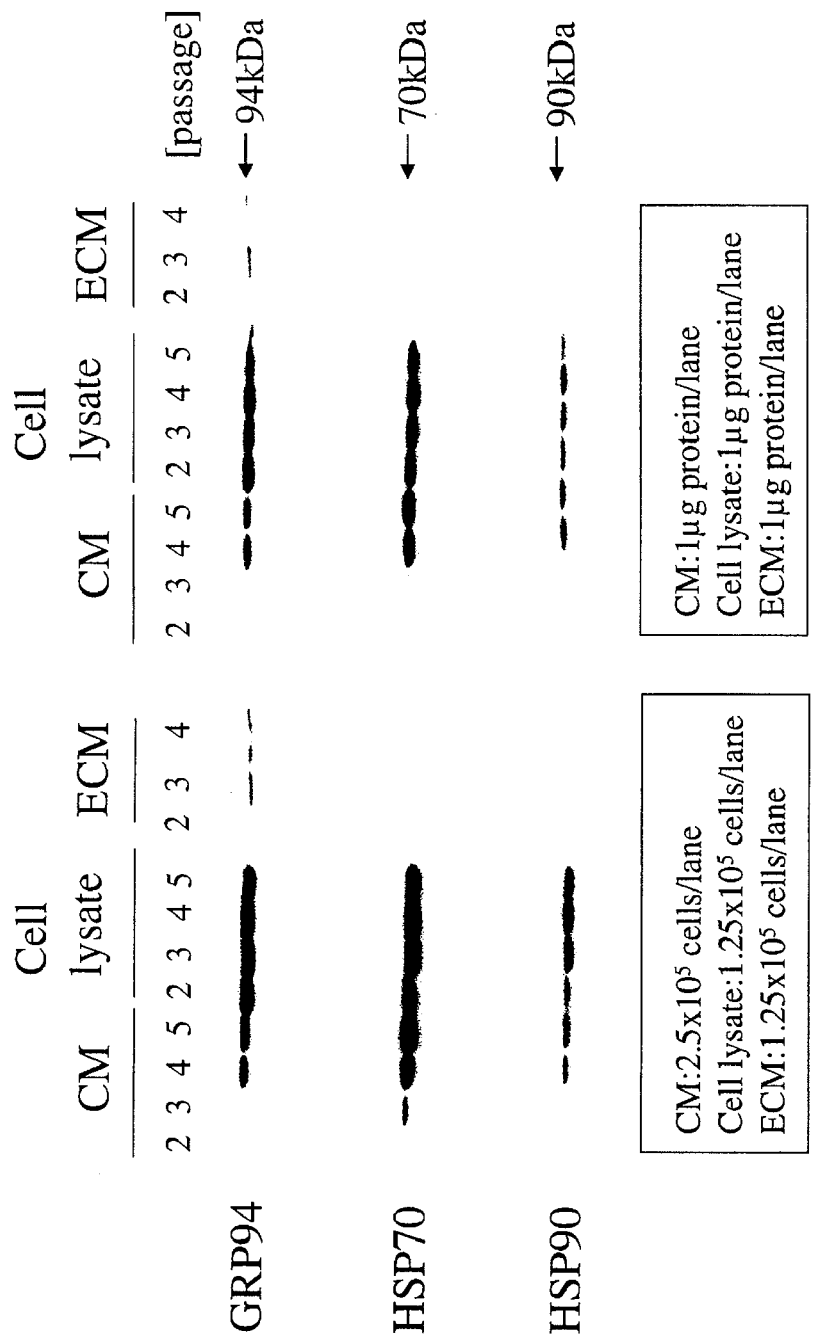
[Fig. 6]

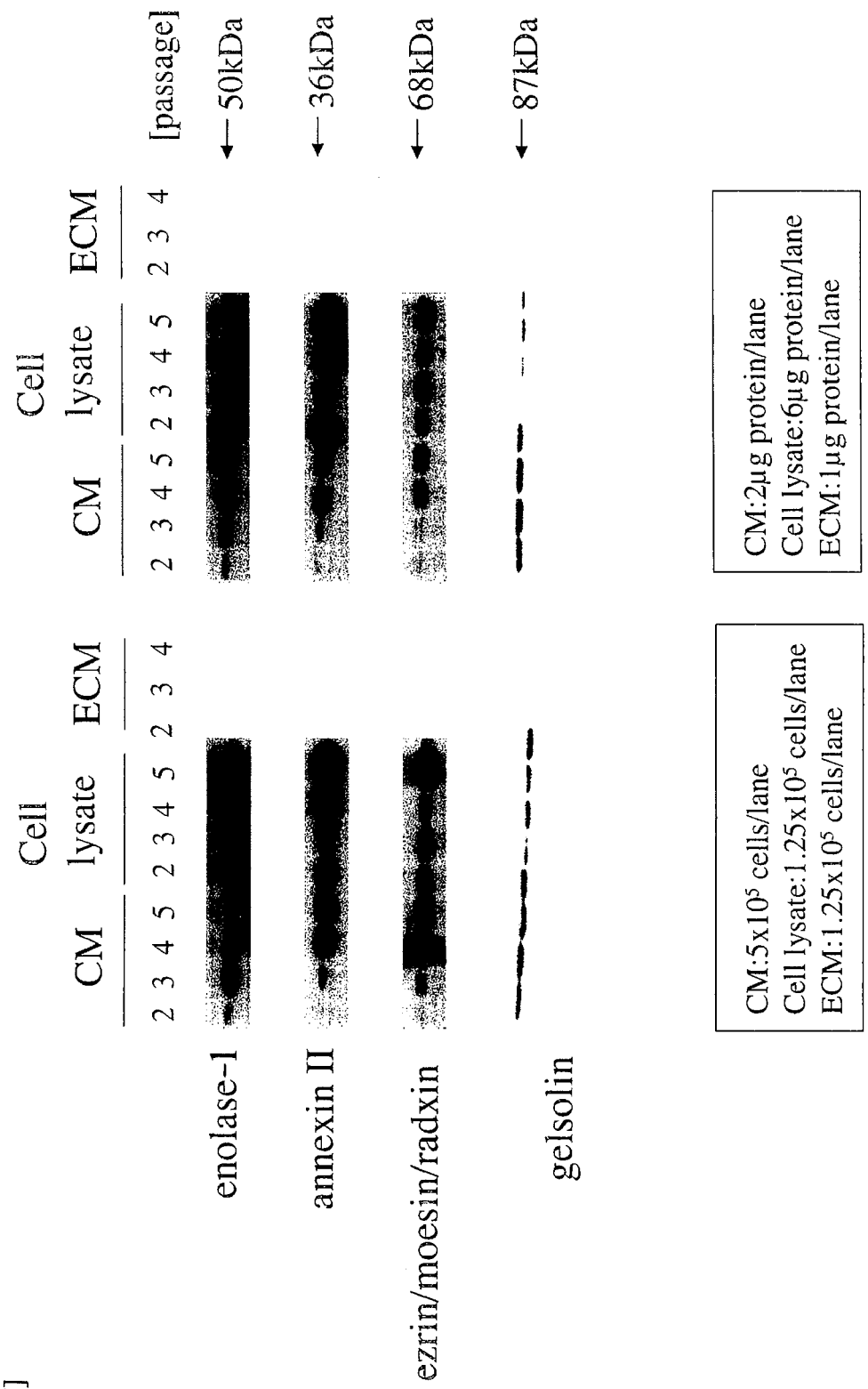
[Fig. 7]

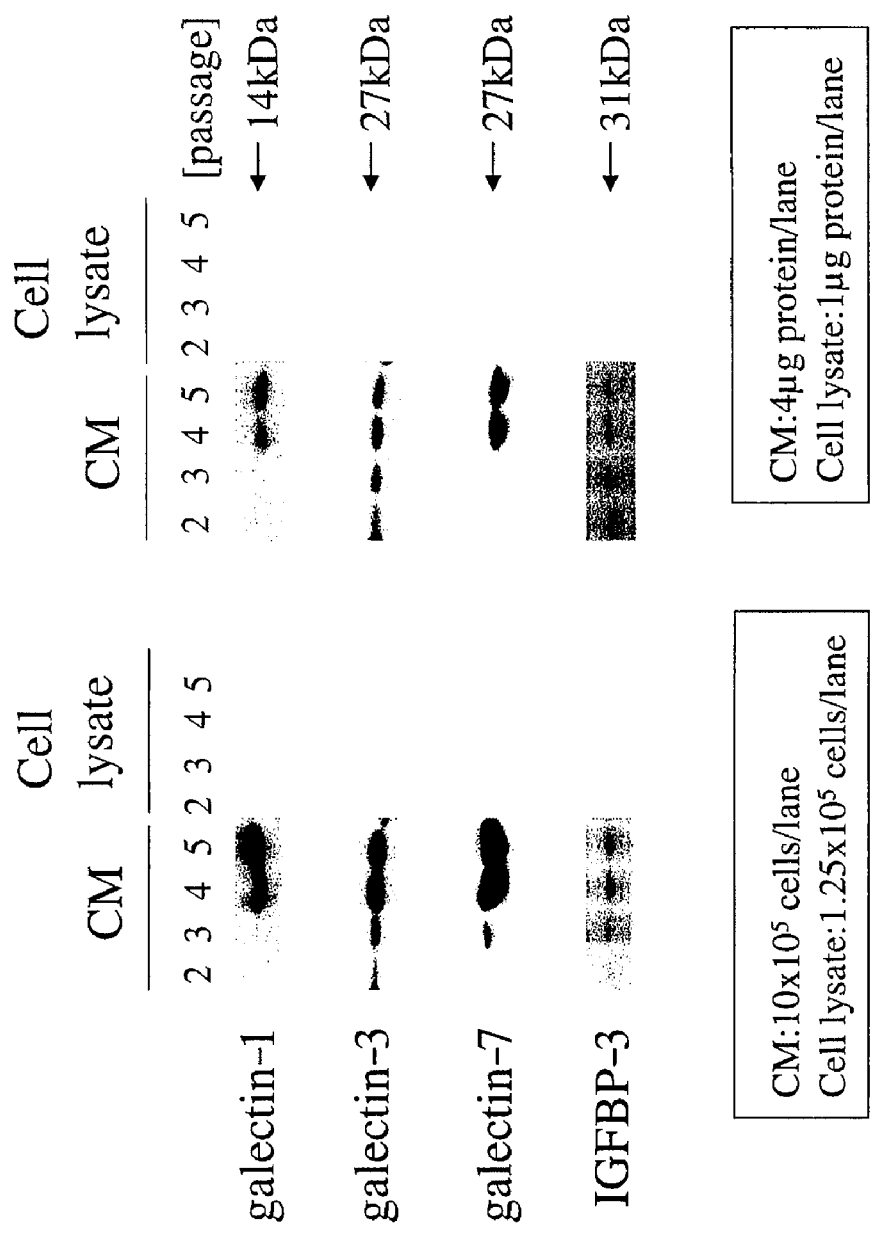
[Fig. 8]

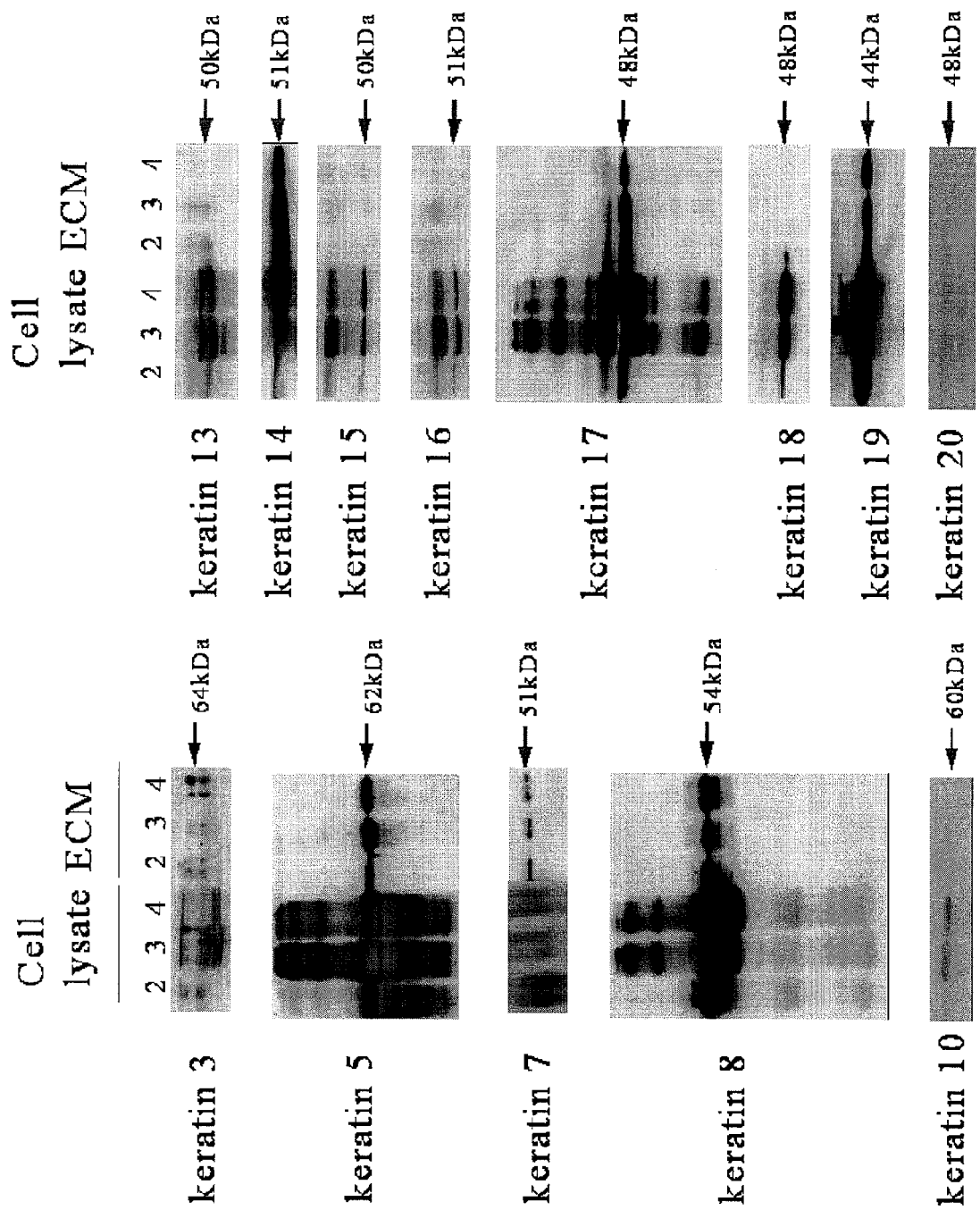
[Fig. 9]

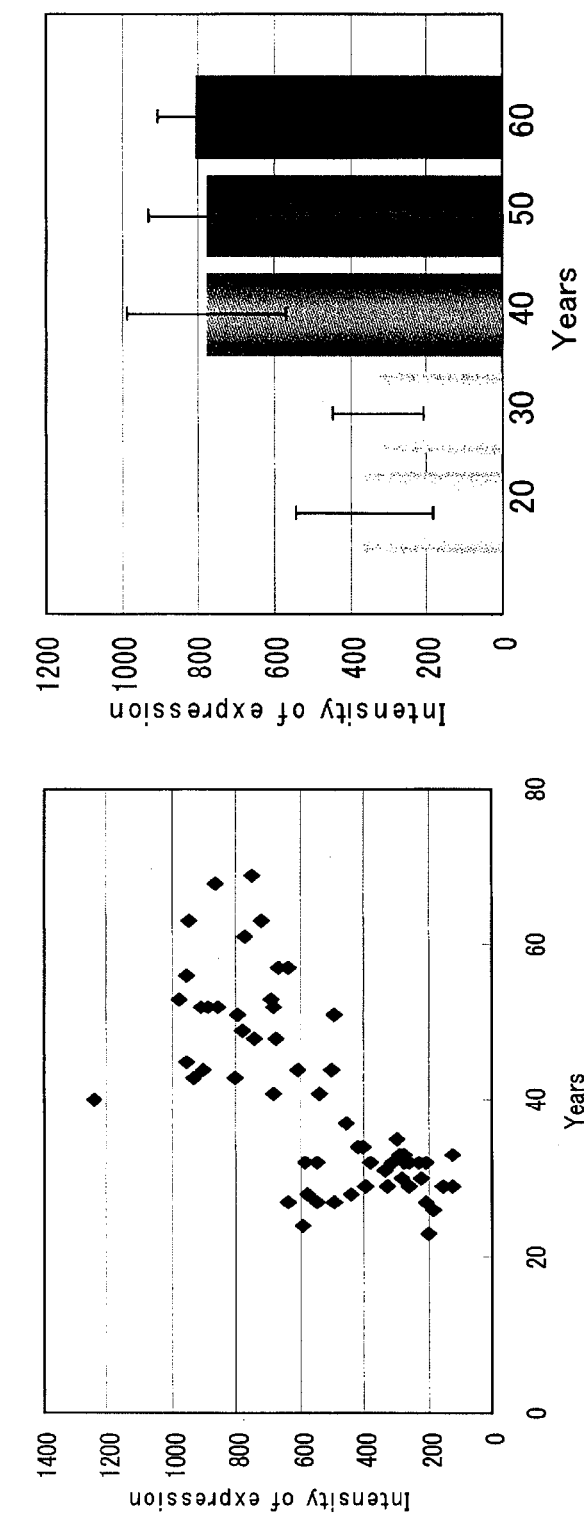
[Fig. 10]

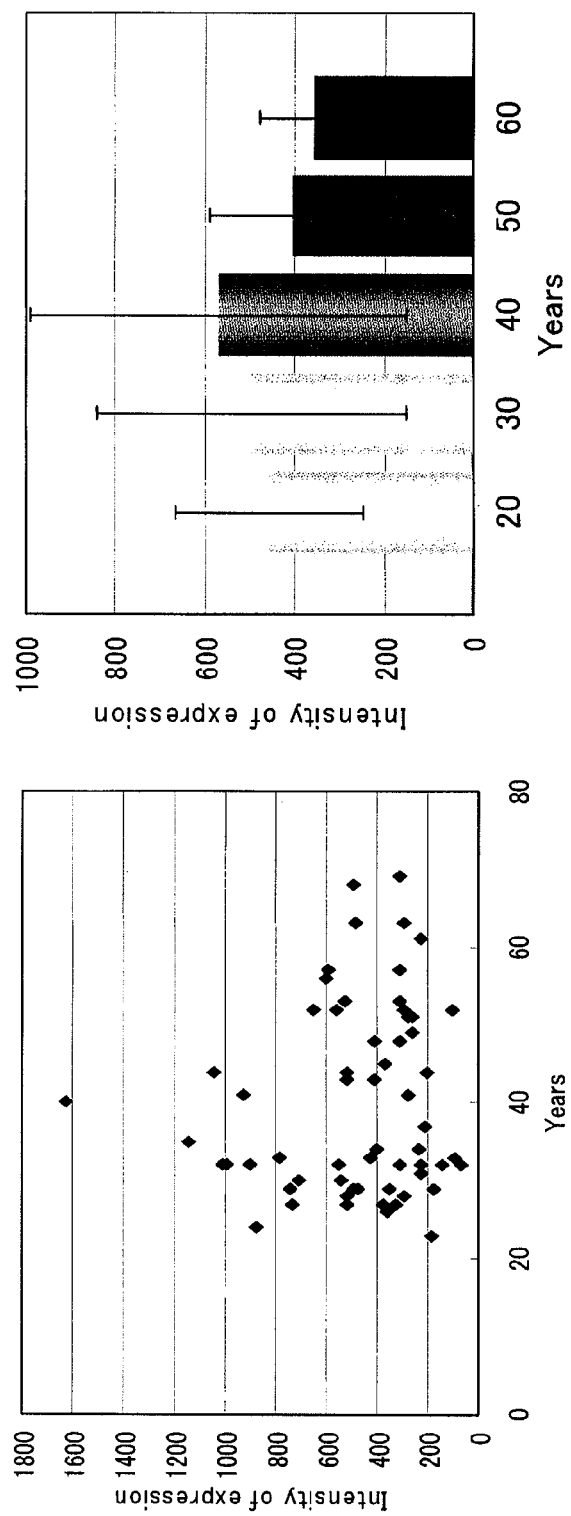
[Fig. 11]

[Fig. 12]
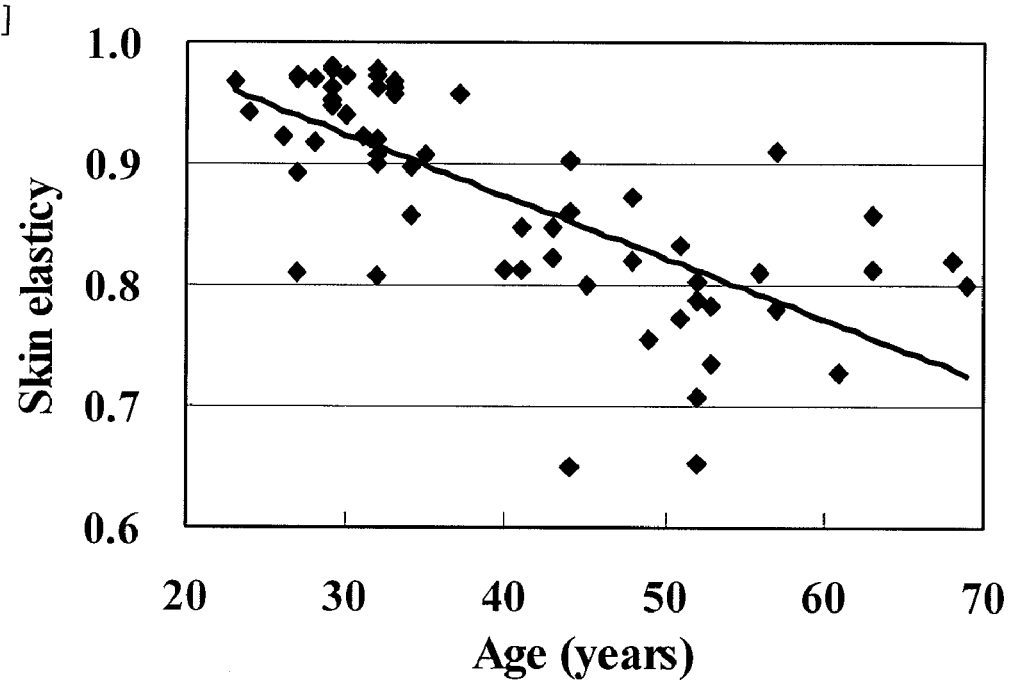
y = -0.0051x + 1.0757, R² = 0.5012, P<0.0001, N=59

[Fig. 13]
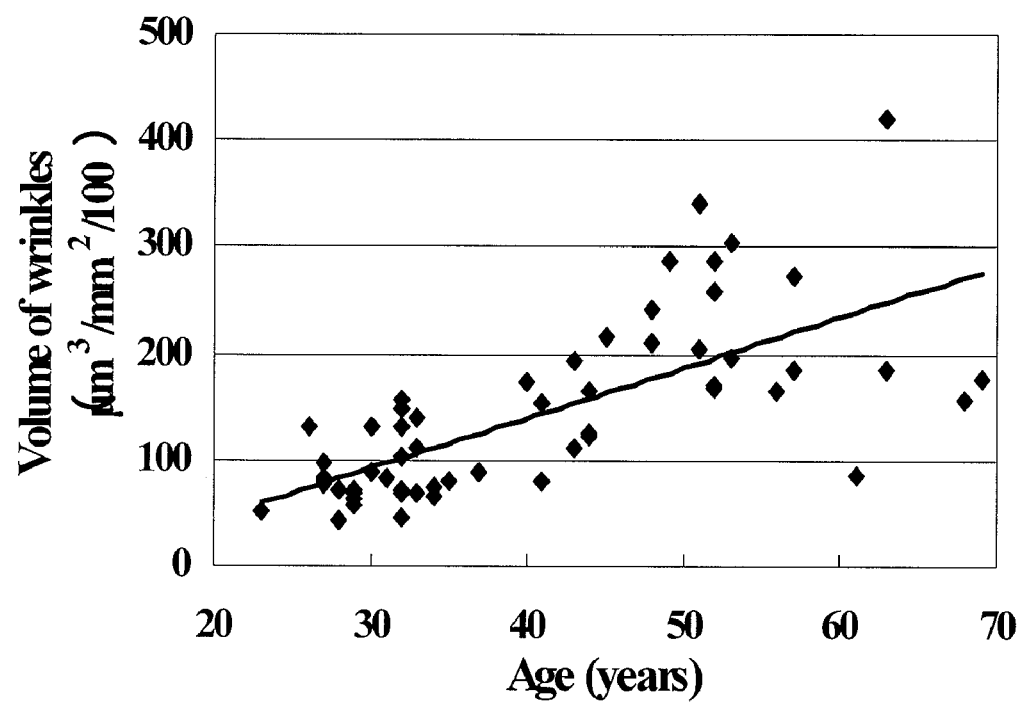
$y = 4.7465x - 50.657$, $R^2 = 0.497$, $P<0.0001$, $N=59$

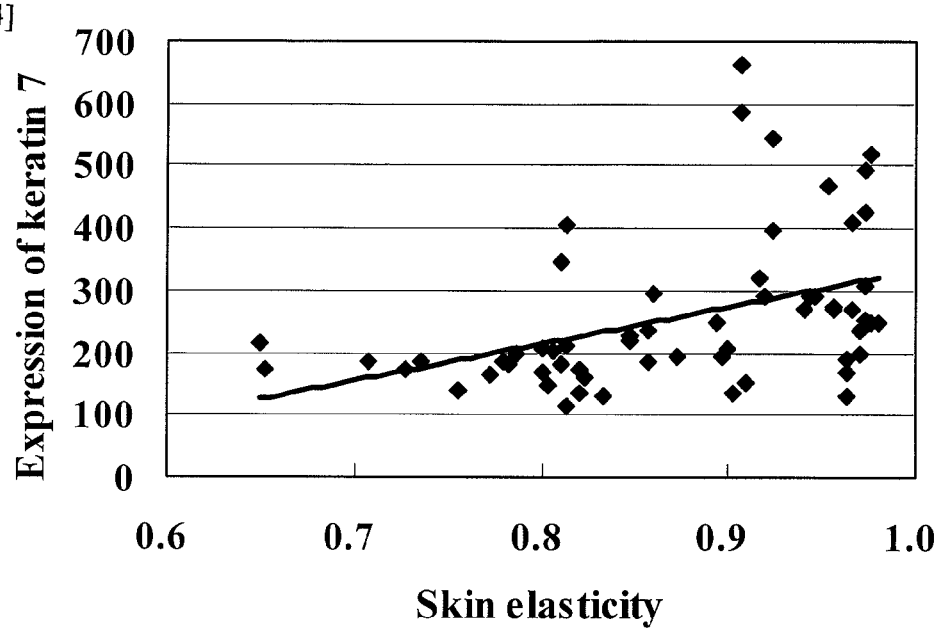
[Fig. 14]
y = 593.66x - 260.82, R² = 0.1806, P<0.001, N=59

[Fig. 15]
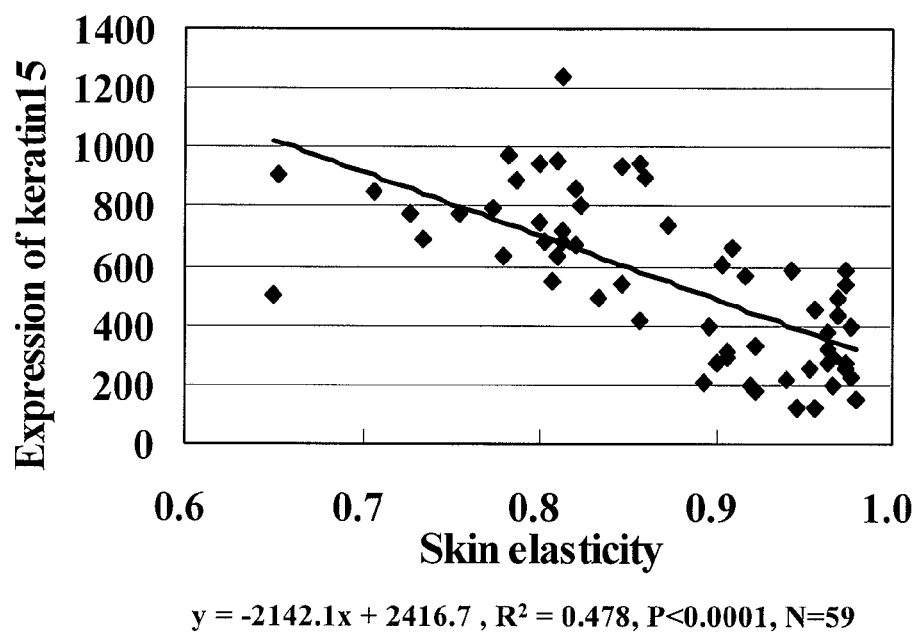
y = -2142.1x + 2416.7 , R² = 0.478, P<0.0001, N=59

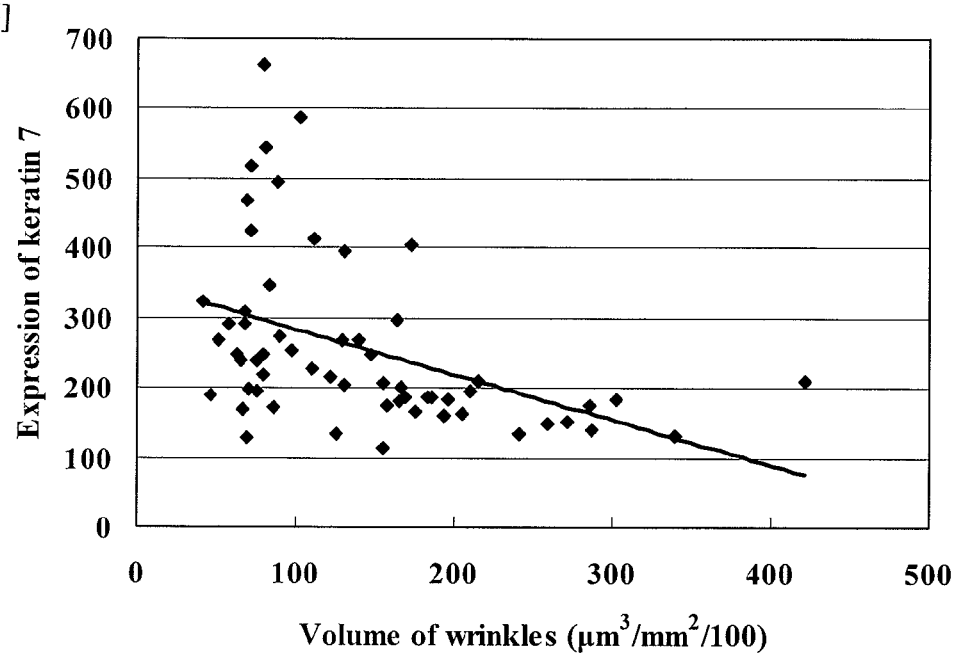
[Fig. 16]
$y = -0.6458x + 347.61$, $R^2 = 0.1837$, $P<0.01$, $N=59$

[Fig. 17]
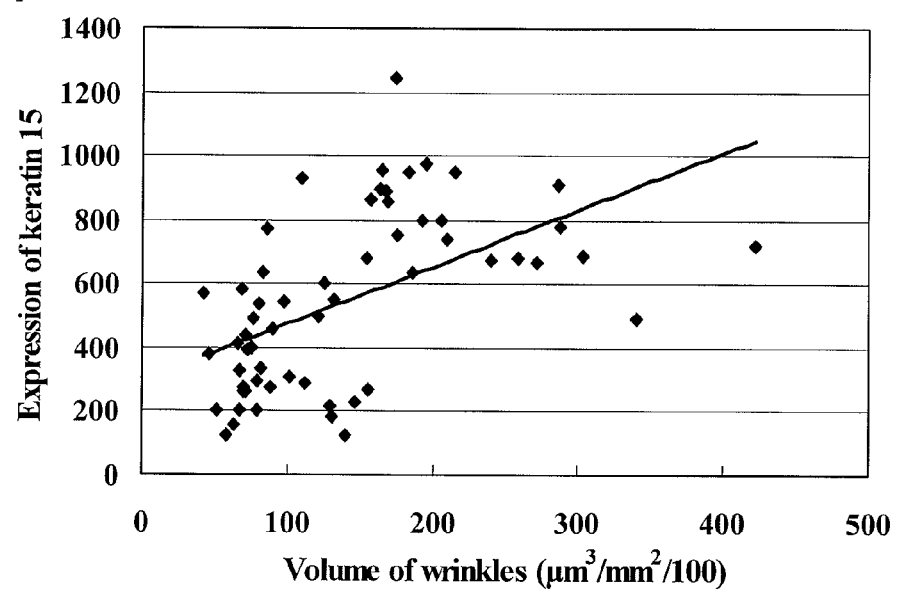
$y = 1.7862x + 295.34$, $R^2 = 0.2853$, $P<0.0001$, $N=59$

[Fig. 18]
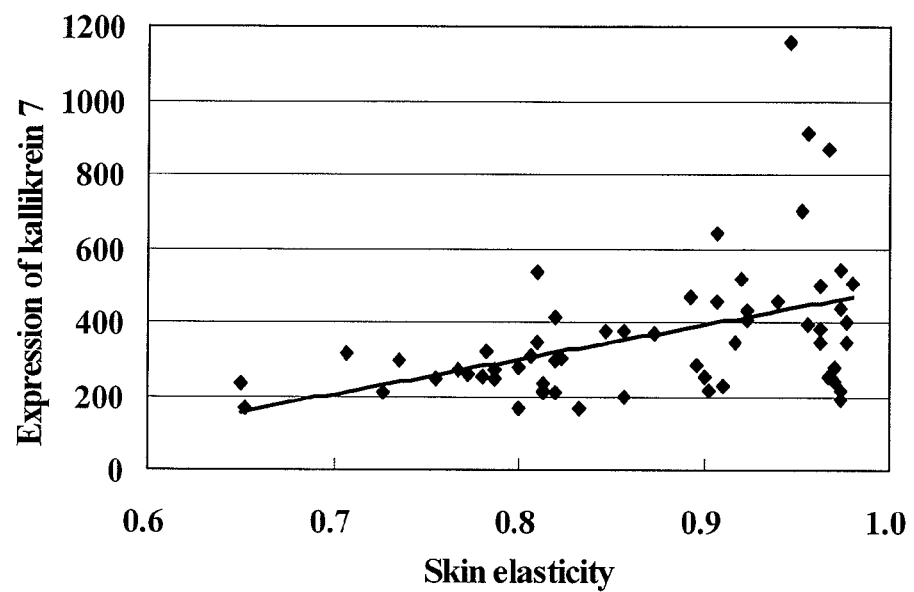
y = 942.55x - 455.75, $R^2$ = 0.1988, P<0.001, N=59

[Fig. 19]
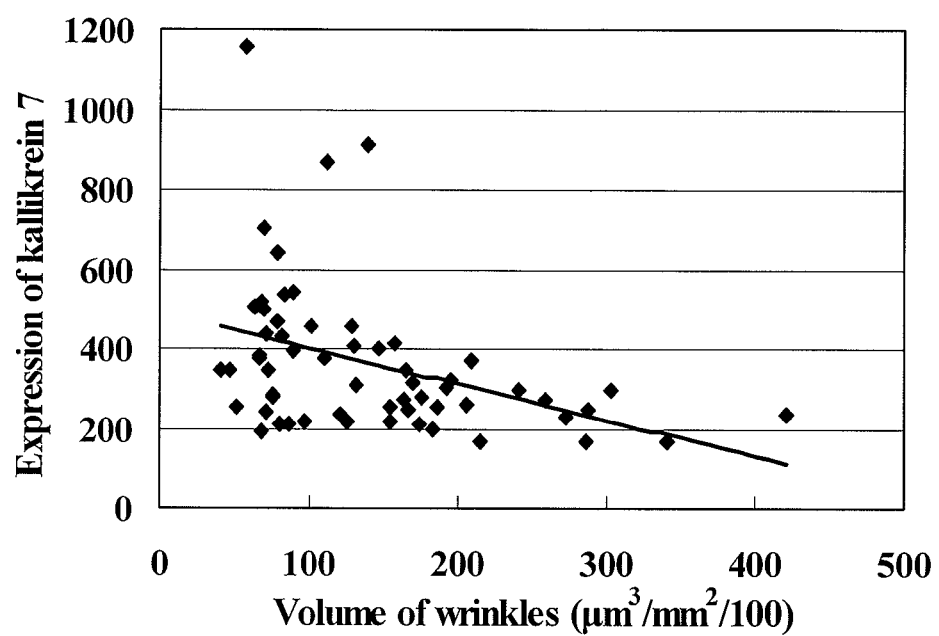
$y = -0.8981x + 489.94$, $R^2 = 0.1516$, $P<0.001$, $N=59$

SKIN AGING MARKER AND TECHNIQUE FOR USE THEREOF

This application is the U.S. National Phase under 35 U.S.C. §371 of International Application PCT/JP2006/316407, filed Aug. 22, 2006, which claims priority to Japanese Patent Application No. 2005-240820, filed Aug. 23, 2005. The International Application was published under PCT Article 21(2) in a language other than English.

TECHNICAL FIELD

The present invention relates to a skin aging marker and its utilization technology.

RELATED ART

Our skin changes with age and these changes are generally recognized as lines, sagging and other visible conditions, and objective evaluations using equipment have been attempted to estimate the skin's age based on apparent changes. Methods that are reported to be actually in use include one that estimates the actual age from the degree of lines and sagging, one that measures the degree of apparent fineness of skin using a fiberscope, etc., and one that determines the skin's age from the change in vibration measured by contacting a vibrator to the skin (Patent Literatures 1 to 3).

Aging of cells has been cited as a cause of aging, but whether aging of cells actually causes aging of an individual has not been substantiated yet. A recent report presents a result substantiating that aging of cells causes aging of an individual (Non-patent Literature 1). When our skin changes with age, it is considered that aging starts at the cellular level before apparent changes occur such as lines and sagging. For example, various factors whose expression changes as the skin ages include decrease in collagen and other extracellular matrix proteins (ECMs), and increase in proteases having the effect of breaking down ECMs (Non-patent Literatures 2 to 4). Abnormal proteins generated in our body, which have been oxidized or otherwise modified, are broken down by proteasomes. However, less proteasomes are expressed in the skin with age and oxidized collagen is stored as a result (Non-patent Literature 5). Accordingly, evaluating only the apparent changes is not enough to accurately measure the degree of skin aging, and it is important to examine the biochemical changes that occur at the cellular level as the skin ages.

Senescence-associated β-galactosidase (SA-β-Gal) has been identified as an aging marker for skin cells, and SA-β-Gal has been shown to express specifically in aged cells, without expressing itself in terminally differentiated cells, and to present a very good correlation with aging of human skin tissues (Non-patent Literature 6). Other skin aging markers that have been reported include Maspin, which is a type of serine protease inhibitor, and Cystatin A, which is a type of cysteine protease inhibitor (Non-patent Literatures 7, 8).

One effective method to find biomarkers for skin aging is to separate all proteins (proteome) present in specific cells under a specific condition using two-dimensional electrophoresis and then identify these proteins using a mass spectrometer (proteomics). In reality, proteins have been extracted from human skin tissues of young and old persons, where the proteins found by proteomics that have changed significantly due to aging of skin include eIF-5A, Cyclophilin A, Proteasomal protein, PA28-α, Tryptophanyl-tRNA synthetase, HSP 60, Annexin I, NM23 H2 (nucleoside diphosphatase kinase), PI3K p85β isoform, Mn-superoxide dismutase, PAI-2, and Mx-A protein (Non-patent Literature 9). However, proteomics studies that have been carried out for skin are analyses using extracts from skin tissues or cell extracts, and there are no examples where proteomics was done by focusing on the supernatant of cell culture containing a lot of proteins secreted in trace amount. Also, verification of identified skin aging markers using human skin involves less practical methods such as immunostaining using skin tissues taken by biopsy, and there are no examples of highly practical methods where expression of skin aging markers was examined by collecting a sample of horny cell layer using a horny cell layer checker, which is capable of collecting a sample of horny cell layer in a non-invasive, safe and simple manner, and then extracting proteins from the collected sample.

Patent Literature 1: Japanese Patent Laid-open No. 2002-330943
Patent Literature 2: Japanese Patent Laid-open No. 2002-360544
Patent Literature 3: Japanese Patent Laid-open No. 2001-212087
Non-patent Literature 1: J. Clinic. Invest., 114, 1299-1307, 2004
Non-patent Literature 2: Mol. Cell. Biochem., 1999 April, 194 (1-2): 99-108
Non-patent Literature 3: J. Investig. Dermatol. Symp. Proc., 3 (2), 172-179, 1998
Non-patent Literature 4: Mech. Ageing Dev., 123 (7), 801-810, 2002
Non-patent Literature 5: J. Gerontology, 55 (5), 220-227, 2000
Non-patent Literature 6: Proc. Natl. Acad. Sci. USA, 92, 9363-9367, 1995
Non-patent Literature 7: Cancer Research, 64, 2956-2961, 2004
Non-patent Literature 8: Dermatology, 188, 21-24, 1994
Non-patent Literature 9: Mol. Cell. Proteomics, 2 (2), 70-84, 2003

SUMMARY OF THE INVENTION

Problems to be Solved by the Invention

It is an object of the present invention to find substances that can be used as skin aging markers.

Means for Solving the Problems

The inventors focused on the supernatant of cell culture containing a lot of proteins secreted in trace amount, and conducted proteomics of proteins whose expression changes with aging of epidermal keratinocytes. To be specific, we conducted proteome analysis using two-dimensional electrophoresis and a mass spectrometer by preparing supernatants of cultures of second passage (young cells) through fifth passage (aged cells) of normal human epidermal keratinocytes. Also, as one unique feature of the present invention, we attempted to identify ultratrace proteins (1 femto-mol or less) using a technology that makes such identification possible (Experimental Medicine, 20 (16), 2367-2370, 2002).

As a result, we were able to identify 19 proteins whose expression decreased with aging of epidermal keratinocytes (Table 1) and 49 proteins whose expression increased (Table 2). These proteins included β2-microglobulin, PAI-1, Kallikrein 7 and other new skin aging markers, in addition to known skin aging markers. Furthermore, we used one-dimensional Western blotting to confirm the expression of proteins identified by proteome analysis and identified several proteins having a correlation with aging of epidermal keratinocytes (Table 3). Since two types of Keratin, which is a cytoskeletal protein, were identified by proteome analysis, we also examined how different types of Keratin would change their expression with aging of epidermal keratinocytes. As a result, eight types of Keratin (Keratin 10, 13, 14, 15, 16, 18, 19 and 20) increased their expression with aging of epidermal keratinocytes, while the expression of Keratin 7 decreased. In addition to the proteins whose expression changed, we also identified β2-microglobulin as a protein that would exhibit a higher ratio of the non-severed type, to the severed type resulting from severing of protein by protease, with aging of epidermal keratinocytes.

Also, we collected samples of horny cell layer from volunteers in their 20s to 60s using a horny cell layer checker capable of collecting a sample of horny cell layer in a non-invasive, safe and simple manner, after which we extracted proteins from the collected samples and examined the expression of skin aging markers using Western blotting in order to examine the correlation between the skin aging markers identified above and the degree of aging of human skin. As a result, it became clear that Keratin 7, Keratin 15 and Kallikrein 7 have a very good correlation with skin elasticity and volumetric ratio of lines, which are known as indicators of skin aging.

The present invention is summarized as follows:

(1) A method for determining the degree of skin aging, including measurement of expression of secretory proteins and/or intracellular proteins and/or their genes in skin cells and/or skin tissues, wherein the secretory proteins and/or intracellular proteins change their expression with aging of skin.

(2) A method according to (1), wherein secretory proteins and/or intracellular proteins are selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

(3) A method according to (1) or (2), wherein expression of secretory proteins and/or intracellular proteins is measured at the protein level.

(4) A method according to (1) or (2), wherein gene expression of secretory proteins and/or intracellular proteins is measured at the RNA level.

(5) A kit for determining the degree of skin aging, including antibodies capable of specifically recognizing secretory proteins and/or intracellular proteins whose expression changes with aging of skin.

(6) A kit according to (5), wherein secretory proteins and/or intracellular proteins are selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

(7) A kit for determining the degree of skin aging, including nucleic acid probes capable of specifically hybridizing with mRNA of secretory proteins and/or intracellular proteins whose expression changes with aging of skin.

(8) A kit according to (7), wherein secretory proteins and/or intracellular proteins are selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

(9) A kit for determining the degree of skin aging, including a pair of nucleic acid primers comprising a nucleic acid primer capable of specifically hybridizing with mRNA of secretory proteins and/or intracellular proteins whose expression changes with aging of skin, and a nucleic acid primer capable of specifically hybridizing with cDNA synthesized using the aforementioned mRNA as a mold.

(10) A kit according to (9), wherein secretory proteins and/or intracellular proteins are selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

(11) A method for identifying substances effective in the prevention of skin aging, including:
  (a) a step to cause a target substance to contact skin cells and/or skin tissues;
  (b) a step to culture for a specified time the skin cells and/or skin tissues caused to contact the target substance in step (a);
  (c) a step to measure the expression of secretory proteins and/or intracellular proteins and/or their genes in the skin cells and/or skin tissues cultured in step (b), wherein the secretory proteins and/or intracellular proteins change their expression with aging of skin; and
  (d) a step to evaluate the effect of the target substance relative to the expression of secretory proteins and/or intracellular proteins and/or their genes in skin cells and/or skin tissues, by comparing the expression of secretory proteins and/or intracellular proteins and/or their genes measured in step (c) against the expression of secretory proteins and/or intracellular proteins and/or their genes in control skin cells and/or skin tissues.

(12) A method according to (11), wherein secretory proteins and/or intracellular proteins are selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

Effects of the Invention

The present invention can establish an evaluation system that uses, as an indicator, change with aging of skin at the cellular level. By using this evaluation system, the degree of skin aging can be determined in a more detailed and accurate manner compared to conventional methods. The present invention also provides a kit for determining the degree of skin aging and a method for identifying substances effective in the prevention of skin aging.

BRIEF DESCRIPTION OF THE DRAWINGS

FIG. 1 Change in proliferation (a) and change in form (b) occurring in passages of epidermal keratinocytes FIG. 2 Stained image of cells stained by SA-β-Gal (a) and percentage of cells stained by SA-β-Gal (b) for each passage of epidermal keratinocytes FIGS. 3(a) to 3(d) Expression patterns, obtained by two-dimensional electrophoresis, of proteins extracted from the second (FIG. 3(a)) and fifth passages (FIG. 3(b)) of epidermal keratinocytes, and tables indicating identified proteins corresponding to spot numbers (FIGS. 3(c) and 3(d))

FIG. 4 Results of analysis, by one-dimensional Western blotting, of change in expression of Laminin 5 and Fibronectin with aging of epidermal keratinocytes FIGS. 5(a), 5(b) Results of analysis, by one-dimensional Western blotting, of change in expression of proteases and protease inhibitors with aging of epidermal keratinocytes FIG. 6 Results of analysis, by one-dimensional Western blotting, of change in expression of heat shock proteins with aging of epidermal keratinocytes FIG. 7 Results of analysis, by one-dimensional Western blotting, of change in expression of intracellular and cytoskeletal proteins with aging of epidermal keratinocytes FIG. 8 Results of analysis, by one-dimensional Western blotting, of change in expression of Galectin and IGFBP-3 with aging of epidermal keratinocytes FIG. 9 Results of analysis, by one-dimensional Western blotting, of change in expression of Keratins with aging of epidermal keratinocytes FIG. 10 Correlation between the aging and the expression of Keratin 15 extracted from the horny cell layer at the corner of the eye FIG. 11 Correlation between the aging and the expression of Keratin 10 extracted from the horny cell layer at the corner of the eye FIG. 12 Correlation between the aging and the elasticity at the corner of the eye FIG. 13 Correlation between the aging and the volumetric ratio of lines at the corner of the eye FIG. 14 Correlation between the elasticity at the corner of the eye and the expression of Keratin 7 extracted from the horny cell layer at the corner of the eye FIG. 15 Correlation between the elasticity at the corner of the eye and the expression of Keratin 15 extracted from the horny cell layer at the corner of the eye FIG. 16 Correlation between the volumetric ratio of lines at the corner of the eye and the expression of Keratin 7 extracted from the horny cell layer at the corner of the eye FIG. 17 Correlation between the volumetric ratio of lines at the corner of the eye and the expression of Keratin 15 extracted from the horny cell layer at the corner of the eye FIG. 18 Correlation between the elasticity at the corner of the eye and the expression of Kallikrein 7 extracted from the horny cell layer at the corner of the eye FIG. 19 Correlation between the volumetric ratio of lines at the corner of the eye and the expression of Kallikrein 7 extracted from the horny cell layer at the corner of the eye

BEST MODE FOR CARRYING OUT THE INVENTION

Figure 3A:
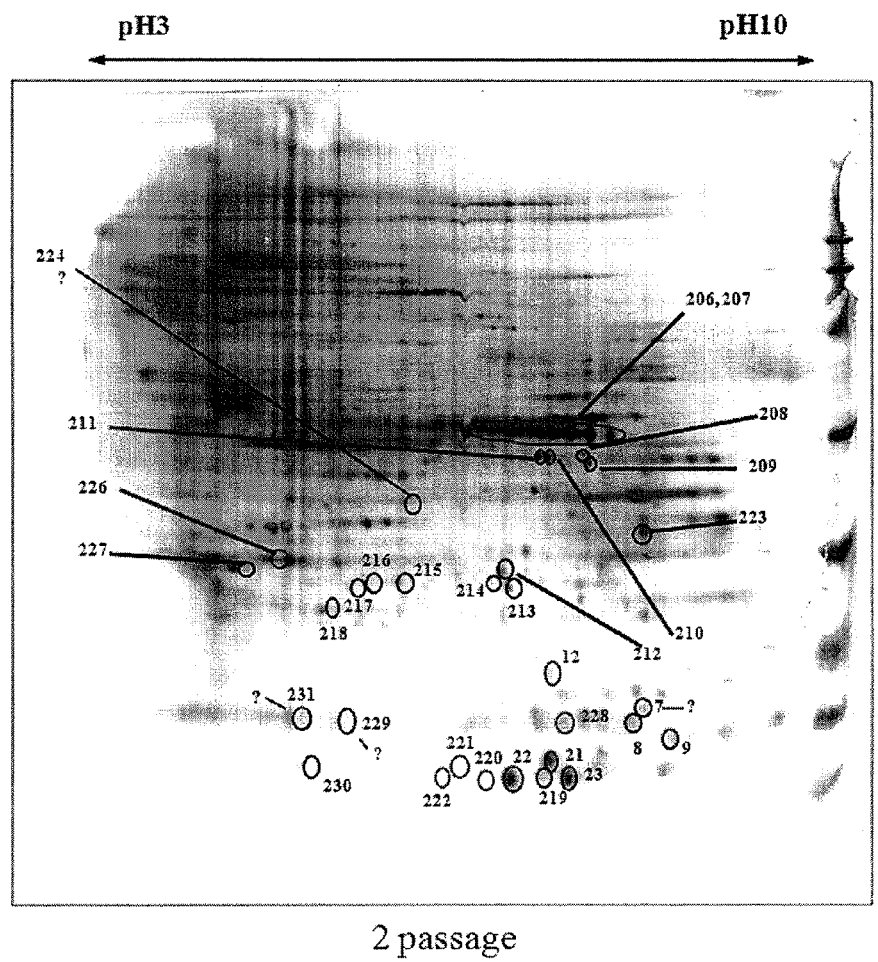

Embodiments of the present invention are explained below in details.

The present invention provides a method for determining the degree of skin aging, including measurement of secretory proteins and/or intracellular proteins in skin cells and/or skin tissues. Secretory proteins and/or intracellular proteins change their expression with aging of skin. Forms of "change in expression" include change in presence/absence of expression of a protein and/or its gene, change in the amount of expression, and change in the ratio of severed and non-severed types of an expressed protein due to protease. Secretory proteins and/or intracellular proteins used to determine the degree of skin aging are preferably selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin. One or more proteins may be selected.

Kallikrein 7 is a secretory protein with a molecular weight of 27,525 Da. It has the effect of promoting the desquamation of cells from the skin surface by severing the intercellular bond in the horny cell layer. Kallikrein 7 is expressed in a large amount in skin tissues, while it is also expressed in the brain, mammary gland, spinal cord and kidney. Gene sequence information (Stratum corneum chymotrytic enzyme, J. Biol. Chem. 269: 19420-19426, 1994, L33404). Amino acid sequence information (Kallikrein 7 precursor, J. Biol. Chem. 269: 19420-19426, 1994, P49862).

PAI-1 is a secretory protein with a molecular weight of 45,060 Da. It is a type of serine protease and inhibits the activation of tPA (tissue plasminogen activator), uPA, protein C, etc. PAI-1 is a glycoprotein having stability against acids and belongs to the serpin family. PAI-1 is found in plasma, platelets, endothelial cells, liver cells, and fibrosarcoma cells. Gene sequence information (Plasminogen activator inhibitor-1, J. Clin. Invest. 78: 1673-1680, 1986, M16006). Amino acid sequence information (Plasminogen activator inhibitor-1, FEBS Lett. 210: 11-16, 1987, P05121).

uPA is a secretory protein with a molecular weight of 48,525 Da. uPA is a type of serine protease that converts plasminogen into plasmine. uPA is secreted extracellularly as a precursor protein (55 kDa) and takes a severed form (35 kDa) to exhibit protease activity. A large amount of uPA is expressed in breast cancer patients. Gene sequence information (Urokinase-type plasminogen activator, Nucleic Acids Res. 13: 2759-2771, 1985, BC013575). Amino acid sequence information (Urokinase-type plasminogen activator, Hoppe-Seyler's Z. Physiol. Chem. 363: 1043-1058, 1982, P00749).

Matriptase is a secretory protein with a molecular weight of 75,626 Da. It is an enzyme that breaks down extracellular matrixes. Matriptase has been reported to play a part in infiltration and metastasis of breast cancer. It exhibits enzyme activity similar to trypsin. It has also been shown that matriptase forms a complex with HAI-1 (Hepatocyte growth factor activation inhibitor 1), which is an inhibitor of matriptase. In addition, studies have shown that mice in which matriptase gene has been knocked will die due to the inability to control moisture evaporation from the skin. Gene sequence information (Membrane-type serine protease 1, J. Biol. Chem. 274: 18231-18236, 1999, AF188224). Amino acid sequence information (Membrane-type serine protease 1, J. Biol. Chem. 274: 18237-18242, 1999, Q9BS01).

GRP 94 is a secretory protein with a molecular weight of 92,469 Da. It is a type of heat shock protein and a chaperon molecule that acts in the severing and transport of secretory proteins. Having a signal peptide, GRP 94 is secreted extracellularly in some situations or localized in ER in others. Gene sequence information (tumor rejection antigen (gp96) 1, Proc. Natl. Acad. Sci. USA. 87: 5658-5662, 1990, BC066656). Amino acid sequence information (Endoplasmin, Nat. Biotechnol. 21: 566-569, 2003, P14625).

HSP 70 is an intracellular protein with a molecular weight of 70,052 Da. Normally it functions as a molecular chaperon in cells and involves in the folding, transport, aggregation and breakdown of proteins, among others. In addition, HSP 70 helps proteins transfer normally in mitochondria and ER. HSP 70 also coordinates with HSP 90 to take part in signal transmission in cells. Gene basal sequence information (Heat shock 70 kDa protein 1A, Immunogenetics 32: 242-251, 1990, BC002453). Amino acid sequence information (Heat shock 70 kDa protein 1, P08107).

HSP 90 is an intracellular protein with a molecular weight of 85,453 Da. Usually it plays an important role in the signal transmission system by bonding with/dissociating from complexes such as steroid hormone receptors. When cells are exposed to high temperature, HSP 90 changes its structure and acts as a molecular chaperon that prevents irreversible damage to proteins. Gene basal sequence information (Heat shock protein 90, Nucleic Acids Res. 17: 7108-710, 1989, X15183). Amino acid sequence information (Heat shock protein 90, J. Biol. Chem. 264: 2431-2437, 1989, P07900).

Galectin-1 is an intracellular protein with a molecular weight of 14,585 Da. It is secreted extracellularly in some situations. Galectin-1 is present in the heart, stomach, skeletal muscles, nerves, thymus gland, kidney, placenta, etc. It bonds with β-galactoside, CD 45, CD 3, CD 4, etc. Galectin-1 is known to promote cell proliferation, induce apoptosis and influence immune response. It also specifically bonds with Laminin, Integrin and other extracellular matrix components and cell receptors to exert significant influence over adhesion and movement of cells. Gene sequence information (Galectin-1, J. Biol. Chem. 264: 1310-1316, 1989, BT006775). Amino acid sequence information (Galectin-1, J. Biochem. 104: 1-4, 1988, P09382).

Galectin-3 is an intracellular protein with a molecular weight of 35,678 Da. It is a galactose-specific lectin that bonds with IgE. Galectin-3 is mainly expressed in the epithelium of large intestine as well as in active macrophages. Galectin-3 is produced by epidermal keratinocytes and present at the surface of islet of Langerhans in the skin, and reportedly bonds with IgE to control the immune system. Gene sequence information (Galectin-3, Proc. Natl. Acad. Sci. USA. 87: 7324-7328, 1990, AB006780). Amino acid sequence information (Galectin-3, P17931).

Galectin-7 is an intracellular protein with a molecular weight of 14,944 Da. Generally it controls cell proliferation between cells or between a cell and an extracellular matrix. Being an apoptosis-related protein, Galectin-7 controls the activation of JNK and release of cytochrome C. It is also secreted in cytoplasm, nucleus and outside cells. Galectin-7 is a member of the galectin sub-family which is the first human epidermis to have been cloned. According to studies of cultured epidermal keratinocytes, Galectin-7 is expressed in all epidermal cells without being affected by the degree of cornification. Gene sequence information (Galectin-7, Dev. Biol. 168: 259-271, 1995, L07769). Amino acid sequence information (Galectin-7, J. Biol. Chem. 270: 5823-5829, 1995, P47929).

IGFBP-3 is a secretory protein with a molecular weight of 31,660 Da. Generally it bonds with IGF to take on a longer half life. In cell cultures, IGFBP-3 suppresses or promotes cell proliferation. At the cell surface, it bonds with IGF receptors. IGFBP-3 has a greater bonding strength with IGF-2 than with IGF-1. IGFBP-3 is expressed in most tissues. Gene sequence information (Insulin-like growth factor binding protein-3, J. Biol. Chem. 265, 12642-12649, 1990, M35878). Amino acid sequence information (Insulin-like growth factor binding protein-3, J. Biol. Chem. 265, 14892-14898, 1990, P17936).

Enolase-1 is an intracellular protein with a molecular weight of 47,038 Da. It exhibits enzyme activity for 2-phospho-D-glycerate=phosphoenolpyruvate+$H_2O$ and acts in the glycolysis system. Enolase-1 is also reported to have a hand in cell proliferation and allergy in some situations. It controls the activation of plasminogens at the cell surface of leukocytes and nerves and is involved in the formation of fibrins. Enolase-1 needs magnesium to form a stable dimer structure. Enolase-1 is localized in cytoplasm, but its homo-dimer forms are also found in cell membrane. α-enolase is expressed in most tissues, while β-enolase and γ-enolase are expressed only in muscle tissues and nerve tissues, respectively. Gene sequence information (Alpha enolase, Proc. Natl. Acad. Sci. USA. 83: 6741-6745, 1986, M14328). Amino acid sequence information (Alpha enolase, Enzyme Protein 48: 37-44, 1995, P06733).

Annexin II is an intracellular protein with a molecular weight of 38,473 Da. According to reports, some are also secreted extracellularly. It is a membrane-binding protein controlled by calcium, and this protein bonds with two calcium ions. Annexin II is localized near cell membrane. Of the two pairs of annexin repeats, one bonds with calcium, while the other bonds with phospholipid. This protein cross-links with phospholipid-bonded actins in cell membrane or proteins in the cytoskeletal system, or activates plasminogens via tPA. Gene basal sequence information (Annexin A2, Gene 95: 243-251, 1990, BC015834). Amino acid sequence information (Annexin A2, J. Biol. Chem. 266: 5169-5176, 1991, P07355).

Ezrin is an intracellular protein with a molecular weight of 69,268 Da. Radixin and Moesin mentioned below are molecules belonging to the same family as Ezrin. Ezrin mainly connects proteins in the cytoskeletal system with cell membrane. It is localized inside the filiform projection called "microvilli" in cell membrane. Ezrin comprises the microvilli of intestinal epithelial cells. It is phosphorylated by tyrosine kinase. Gene sequence information (Ezrin, J. Biol. Chem. 264: 16727-16732, 1989, X51521). Amino acid sequence information (Ezrin, Biochem. Biophys. Res. Commun. 224: 666-674, 1996, P15311).

Radixin is an intracellular protein with a molecular weight of 68,564 Da. It mainly connects proteins in the cytoskeletal system with cell membrane. Gene sequence information (Radixin, Genomics 16: 199-206, 1993, L02320). Amino acid sequence information (Radixin, P35241).

Moesin is an intracellular protein with a molecular weight of 67,689 Da. It mainly connects proteins in the cytoskeletal system with cell membrane. Moesin expression reportedly decreases in abnormally differentiated epidermal keratinocytes. Gene sequence information (Moesin, Proc. Natl. Acad. Sci. USA. 88: 8297-8301, 1991, M69066). Amino acid sequence information (Moesin, Proc. Natl. Acad. Sci. USA. 88: 8297-8301, 1991, P26038).

Gelsolin is a secretory protein with a molecular weight of 85,698 Da. There are two types: one secreted extracellularly and the other functioning intracellularly. Extracellularly secreted Gelsolin bonds with fibronectin. Gelsolin has three actin polymerization adjustment functions including promotion of actin fiber growth via formation of polymerized nucleus, severing of actin fiber, and protection of severed end of actin fiber. Genlsolin controls both the polymerization and depolymerization phases using these two-sided functions and plays an important role in cell movement. Gelsolin is expressed in large amounts in platelets and fibroblasts. Gene sequence information (Gelsolin, Nat. 323, 455-458, 1986, X04412). Amino acid sequence information (Gelsolin, Nat. Biotechnol. 21, 566-569, 2003, P06396).

Keratin 7 is a cytoskeletal protein with a molecular weight of 51,287 Da and also a component of intermediate filament. It is expressed in various epithelial cells including gland cells. Keratin 7 is also expressed in the transitional epithelium of urinal tract, bile duct, lung, and epithelium of mammary gland. It is used as a tumor marker in some forms. Gene sequence information (Keratin 7, J. Cell Biol. 107: 1337-

1350, 1988, AF509887). Amino acid sequence information (Keratin, type II cytoskeletal 7, P08729).

Keratin 10 is a cytoskeletal protein with a molecular weight of 59,519 Da. It is a component of intermediate filament forming a hetero-tetramer with Keratin 1. Keratin 10 is expressed across the skin, but prominently in the prickle cell layer. Gene sequence information (Keratin 10, J. Mol. Biol. 204: 841-856, 1988, M19156). Amino acid sequence information (Keratin, type I cytoskeletal 10, Electrophoresis 13: 960-969, 1992, P13645).

Keratin 13 is a cytoskeletal protein with a molecular weight of 49,586 Da. It is a component of intermediate filament forming a hetero-tetramer with Keratin 4. Keratin 13 is expressed in the tongue, esophagus, epithelium, and epithelium of urinal tract, among others. Gene sequence information (Keratin 13, Gene 215: 269-279, 1998, X52426). Amino acid sequence information (Keratin, type I cytoskeletal 13, P13646).

Keratin 14 is a cytoskeletal protein with a molecular weight of 51,490 Da. It is a component of intermediate filament forming a hetero-tetramer with Keratin 5. Keratin 14 is present in the epithelium and particularly expressed in large amounts near the basal layer. It is also used as an undifferentiated marker for the epithelium. Gene sequence information (Keratin 14, Proc. Natl. Acad. Sci. USA. 82: 1609-1613, 1985, BC002690). Amino acid sequence information (Keratin, type I cytoskeletal 14, P02533).

Keratin 15 is a cytoskeletal protein with a molecular weight of 49,167 Da. It is a component of intermediate filament. Keratin 15 is mainly localized in the basal layer of epithelium. Gene sequence information (Keratin 15, J. Cell Biol. 106: 1249-1261, 1988, X07696). Amino acid sequence information (Keratin, type I cytoskeletal 15, P19012).

Keratin 16 is a cytoskeletal protein with a molecular weight of 51,136 Da. It is a component of intermediate filament forming a hetero-tetramer with Keratin 6. It is expressed in hair follicles, nails, flat epithelium layer in the oral cavity, basal layer of epithelium, epithelium of palma manus, and sweat glands. Keratin 16 is involved in the proliferation and differentiation of cells. Gene sequence information (Keratin 16, Biochem. Biophys. Res. Commun. 215: 517-523, 1995, AF061812). Amino acid sequence information (Keratin, type I cytoskeletal 16, Electrophoresis 13: 960-969, 1992, P08779).

Keratin 18 is a cytoskeletal protein with a molecular weight of 47,926 Da. It is a component of intermediate filament forming a hetero-tetramer with Keratin 8. Keratin 18 is present in the epithelium of most single layer glands. Patients lacking Keratin 18 have risks of developing a sudden hepatic failure. Gene sequence information (Keratin 18, Differentiation 33: 61-68, 1986, M26325). Amino acid sequence information (Keratin, type I cytoskeletal 18, Electrophoresis 18: 605-613, 1997, P05783).

Keratin 19 is a cytoskeletal protein with a molecular weight of 44,106 Da. It is the smallest form of Keratin in terms of molecular weight. Keratin 19 is a component of intermediate filament. It is expressed in large amounts in most forms of single layer epithelium and non-cornified stratified epithelium. Keratin 19 is also expressed in all types of adenocarcinoma. Gene sequence information (Keratin 19, J. Invest. Dermatol. 92: 707-716, 1989, Y00503). Amino acid sequence information (Keratin, type I cytoskeletal 19, Electrophoresis 13: 960-969, 1992, P08727).

Keratin 20 is a cytoskeletal protein with a molecular weight of 48,486 Da. It is a component of intermediate filament. Among normal cells, Keratin 20 is present in endocrine cells in the epithelium of intestinal tract, epithelium of digestive tract and upper part of gastropyloric, as well as in Merkel cells in the epithelium of urinal tract and skin. Keratin 20 is used as a specific marker protein for colon cancer, etc. Gene sequence information (Keratin 20, Differentiation 53: 75-93, 1993, BC031559). Amino acid sequence information (Keratin, type I cytoskeletal 20, P35900).

$\beta$2-microglobulin is a secretory protein with a molecular weight of 13,175 Da. It is the L chain in HLA class I antigens (histocompatible antigens). $\beta$2-microglobulin is present at the surface of many cells. It is used as a diagnostic indicator for renal failure and various types of malignant tumors, etc. Although $\beta$2-microglobulin in severed form is found in some cases, what it means is not very clear. Gene sequence information (Beta-2-microglobulin, J. Immunol. 139: 3132-3138, 1987, AB021288). Amino acid sequence information (Beta-2-microglobulin, Biochemistry 12: 4811-4822 (1973), P61769).

The above proteins may be a precursor protein or mature protein, or of severed type or non-severed type. Examples of precursor proteins include pro-proteins and prepro-proteins, among others. Some pro-proteins and prepro-proteins have a signal peptide, which is a specific secretory protein sequence.

Under the method proposed by the present invention, expression of secretory proteins and/or intracellular proteins in skin cells and/or skin tissues may be measured or expression of their genes may be measured. For example, such measurement can be performed using the Northern blotting method, PCR method, Western blotting method, immunohistochemical analysis method, etc. Alternatively, cDNA microarray, ELISA method, antibody array, etc., can also be used to perform measurement.

To measure expression of secretory proteins and/or intracellular proteins at the protein level, it is effective to use an antibody that specifically recognizes the target protein. This antibody may be a monoclonal antibody or polyclonal antibody. These antibodies can be manufactured by known methods and some are commercially available. If the Western blotting method is used to perform measurement, the antibody is secondarily detected using $^{125}$I labeled protein A, peroxidase-binding IgG, etc. If measurement is performed using the immunohistochemical analysis method, the antibody are preferably labeled with a fluorochrome, ferritin, enzyme, etc.

To measure gene expression of secretory proteins and/or intracellular proteins at the RNA level, it is effective to use a nucleic acid probe capable of specifically hybridizing with mRNA of the target protein (if the Northern blotting method is used to perform measurement). Alternatively, a pair of nucleic acid primers may be used, including a nucleic acid primer specifically hybridizing with mRNA of the target protein, and a nucleic acid primer capable of specifically hybridizing with cDNA synthesized using the aforementioned mRNA as a mold (if the PCR method is used to perform measurement). Nucleic acid probes and primers can be designed based on the gene information of the target protein. Normally, nucleic acid probes having a basicity of approx. 15 to 1500 are appropriate. Nucleic acid probes are preferably labeled with a radioactive element, fluorochrome, enzyme, etc. Normally, nucleic acid primers having a basicity of approx. 15 to 30 are appropriate.

Under the present invention, presence/absence of expression of secretory proteins and/or intracellular proteins or their genes in skin cells and/or skin tissues may be detected or the amount of expression may be measured. Presence/absence of expression of proteins and/or their mRNA can be checked from presence/absence of appearance of spots and bands at specified locations. The amount of expression of proteins and/or their mRNA can be measured using the staining intensity of spots and bands. Alternatively, proteins and/or their mRNA may be quantified. To measure multiple gene expressions or multiple protein expressions simultaneously, use of such detection methods as DNA array (with the probe fixed on the substrate) (Nature Reviews, Drug Discovery, Volume 1, December 2002, 951-960), protein chip (with the antibody fixed on the substrate) (Nature Reviews, Drug Discovery, Volume 1, September 2002, 683-695), and Luminex (Nature Reviews, Drug Discovery, Volume 1, June 2002, 447-456), is preferred.

Skin cells and skin tissues may be derived from any life form, where examples include those derived from human, pig, monkey, chimpanzee, dog, cow, rabbit, rat, mouse and other mammals. To determine the degree of aging of human skin, however, human-derived tissues need to be used.

Under the method proposed by the present invention, skin biopsy samples, or cultured skin cells, cultured skin tissues and the like, obtained from skin biopsy samples, can be used to determine the degree of skin aging.

Examples of skin cells include epidermal keratinocytes, skin fibroblasts, Langerhans cells, melanin cells, mast cells, endothelial cells, sebum cells, hair papilla cells and hair matrix cells, among others. Skin cells are supplied from the Health Science Research Resources Bank and RIKEN Cell Bank in Japan, or from the American Type Culture Collection outside Japan. They can also be purchased from Clontech, Kurabo and PromoCell. It is also possible to collect skin cells from skin using known methods (*Bunshi Seibutsugaku Kenkyu no Tameno Shin Saibobaiyo Jikkenho* (New Experimental Cell Culture Methods for Molecular Biology Research), p. 57-71, Yodosha, 1999).

Examples of skin tissues include horny cell layer, epidermis and dermis of skin, among others. Skin tissues can be purchased from Biochain and Super Bio Chips. It is also possible to collect skin tissues from skin using known methods (Acta. Derm. Venereol., 85, 389-393, 2005).

Skin models are sold by Kurabo, Toyobo, etc., and these commercially available models can be used. Models can also be fabricated from known methods (J. Invest. Dermatol., 104 (1), 107-112, 1995).

Skin biopsy samples may be cells or tissues. Skin biopsy samples are preferably those of the skin's horny cell layer collected by a horny cell layer checker or other tapes, as described later in examples. Horny cell layer checkers measure the degree of parakeratosis and cell area of the horny cell layer, and have been used for many years in the collection of samples of horny cell layer for the purpose of evaluating the degree of skin roughness and turnover rate of horny cell layer (*Keshohin no Yuyosei: Hyoka Gijutsu no Shimpo to Shorai Tembo* (Utility of Cosmetics: Progress and Future Perspective of Evaluation Technologies), Society of Cosmetic Chemists of Japan, Yakuji Nippo, p 95-96). These checkers are very useful in collecting samples from the horny cell layer in a non-invasive, easy and safe manner at a counseling outlet or home.

The degree of skin aging refers to the degree of aging signs exhibited by the skin such as lines and sagging due to age. It is obvious that lines and sagging progress with age. In addition to age, exposure to UV rays also worsens lines, sagging, dull complexion and pigmentation. Lines and sagging can be measured using known methods (*Keshohin no Yuyosei: Hyoka Gijutsu no Shimpo to Shorai Tembo* (Utility of Cosmetics: Progress and Future Perspective of Evaluation Technologies: Progress and Future Perspective of Evaluation Technologies), Society of Cosmetic Chemists of Japan, Yakuji Nippo, 154-158, 169-175, 179-182, 187-190, 2001).

It is also known that when the skin starts to form lines or sag with age, the ability of epidermal cells, skin fibroblasts and other skin cells to proliferate weakens in the skin. Accordingly, the degree of skin aging can be determined using, as an indicator, drop in the proliferation ability of skin cells. As an example, senescence-associated β-galactosidase (SA-β-Gal) increases in epidermal keratinocytes and skin fibroblasts that have been aged through repeated passages of culture, and this increase in SA-β-Gal is correlated with aging of human skin (Proc. Natl. Acad. Sci. USA., 92, 9363-9367, 1995). Accordingly, it is highly likely that the various proteins identified using epidermal keratinocytes aged through repeated passages of culture may be used as markers for human skin aging.

As an example of the present invention, the degree of skin aging can be determined using the standards explained below.

As shown by the sample analysis of Keratin 7, Keratin 15 and Kallikrein 7 in Example 2, skin samples are obtained from volunteers in different age groups and the amount of expression is measured for specific marker proteins to create standard curves showing the relationships of measured amounts of expression with skin elasticity and degree of lines that are known as indicators of skin aging. The degree of skin aging is determined for analysis samples by comparing the amounts of expressions of standard samples and analysis samples. As for β2-microglobulin, skin samples are obtained from volunteers in different age groups and the average ratio of severed and non-severed types is calculated before creating standard curves showing the relationships of measured amounts of expression with skin elasticity and degree of lines that are known as indicators of skin aging. The degree of skin aging is determined for analysis samples by comparing the amounts of expressions of standard samples and analysis samples.

The present invention also provides a kit for determining the degree of skin aging.

As an example, a kit conforming to the present invention includes antibodies capable of specifically recognizing secretory proteins and/or intracellular proteins whose expression changes with aging of skin. Secretory proteins and/or intracellular proteins are preferably selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin. The kit may also include a tape for collecting skin tissues, a set of reagents for immunochemically detecting the proteins collected on the tape, and an operating manual, among others. Preferably, the operating manual includes description of, among others, how to use the kit, as well as the judgment criteria for determining the degree of skin aging.

In another example, a kit conforming to the present invention includes nucleic acid probes capable of specifically hybridizing with mRNA of secretory proteins and/or intracellular proteins whose expression changes with aging of skin. Secretory proteins and/or intracellular proteins are preferably selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin. The kit may also include a tape for collecting skin tissues, reagents for extracting RNA from the skin tissues collected on the tape, reagents for analyzing RNA using the Northern blotting method, and an operating manual, among others. Preferably, the operating manual includes description of, among others, how to use the kit, as well as the judgment criteria for determining the degree of skin aging.

In yet another example, a kit conforming to the present invention includes a pair of nucleic acid primers comprising a nucleic acid primer capable of specifically hybridizing with mRNA of secretory proteins and/or intracellular proteins whose expression changes with aging of skin, and a nucleic acid primer capable of specifically hybridizing with cDNA synthesized using the aforementioned mRNA as a mold. Secretory proteins and/or intracellular proteins are preferably selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin. The kit may also include a tape for collecting skin tissues, reagents for extracting RNA from the skin tissues collected on the tape, reagents for analyzing RNA using the RT-PCR method, and an operating manual, among others. Preferably, the operating manual includes description of, among others, how to use the kit, as well as the judgment criteria for determining the degree of skin aging.

The present invention also provides a method for identifying substances effective in the prevention of skin aging. This method includes the following steps:

(a) a step to cause a target substance to contact skin cells and/or skin tissues;
(b) a step to culture for a specified time the skin cells and/or skin tissues caused to contact the target substance in step (a);
(c) a step to measure the expression of secretory proteins and/or intracellular proteins in the skin cells and/or skin tissues cultured in step (b), wherein the secretory proteins and/or intracellular proteins change their expression with aging of skin; and
(d) a step to evaluate the effect of the target substance relative to the expression of secretory proteins and/or intracellular proteins in skin cells and/or skin tissues, by comparing the expression of secretory proteins and/or intracellular proteins measured in step (c) against the expression of secretory proteins and/or intracellular proteins in control skin cells and/or skin tissues.

The target substance may be any substance, such as a protein, peptide, vitamin, hormone, polysaccharide, oligosaccharide, monosaccharide, low-molecular compound, nucleic acid (DNA, RNA, oligonucleotide, mononucleotide, etc.), lipid, other natural compound, synthetic compound, or any mixture thereof.

Skin cells and skin tissues have been explained above.

The target substance may be caused to contact skin cells and/or skin tissues using any method, such as a method to add the target substance in a culture solution of skin cells and/or skin tissues, or a method to culture skin cells and/or skin tissues in a culture container or on a culture sheet on which the target substance has been applied or fixed. It is also possible to use a method to apply the target substance directly over the skin, or orally administer the target substance, using a life form such as human or other mammal (such as mouse, rat, guinea pig, rabbit, pig, etc.).

The culture time of skin cells and/or skin tissues is not specifically limited, and a desired time can be set as long as it is enough to check whether the target substance has any effect on the expression of secretory proteins and/or intracellular proteins or their genes in skin cells and/or skin tissues. If normal human epidermal keratinocytes are used as skin cells, for example, a culture time of 12 to 48 hours is appropriate, and that of 12 to 24 hours is preferable. Here, "culture skin cells and/or skin tissues" means growing/proliferating skin cells and/or skin tissues, and the definition also encompasses sustaining the life of, breeding and rearing life forms having skin cells or skin tissues in addition to growing/proliferating isolated single skin cells and/or skin tissues.

The control skin cells and/or skin tissues to be compared against may be skin cells and/or skin tissues not yet contacted by the target substance, or skin cells and/or skin tissues that have been given the same treatment except that they do not contact the target substance.

Secretory proteins and/or intracellular proteins are preferably selected from the group consisting of Kallikrein 7, PAI-1, uPA, Matriptase, GRP 94, HSP 70, HSP 90, Galectin-1, Galectin-3, Galectin-7, IGFBP-3, Enolase-1, Annexin II, Ezrin, Radixin, Moesin, Gelsolin, Keratin 7, Keratin 10, Keratin 13, Keratin 14, Keratin 15, Keratin 16, Keratin 18, Keratin 19, Keratin 20 and β2-microglobulin.

In an example of the present invention, attention is given to the fact that the amount of expression increases for GRP 94, HSP 70, HSP 90, Galectin-1, Galectin-3, Galectin-7, IGFBP-3, Enolase-1, Annexin II, Ezrin, Radixin, Moesin, Gelsolin, Keratin 10, Keratin 13, Keratin 14, Keratin 15, Keratin 16, Keratin 18, Keratin 19 and Keratin 20 with aging of epidermal keratinocytes. Accordingly, if the amount of expression of any of these marker proteins has decreased compared to the control in the skin cells and/or skin tissues contacted by the target substance, and the target substance can be evaluated to have the effect of decreasing the expression of the marker protein, then the target substance can be identified as being a substance effective in the prevention of skin aging.

In another example of the present invention, attention is given to the fact that the amount of expression decreases for Kallikrein 7, PAI-1, uPA, Matriptase and Keratin 7 with aging of epidermal keratinocytes. Accordingly, if the amount of expression of any of these marker proteins has increased compared to the control in the skin cells and/or skin tissues contacted by the target substance, and the target substance can be evaluated to have the effect of increasing the expression of the marker protein, then the target substance can be identified as being a substance effective in the prevention of skin aging.

In yet another example of the present invention, attention is given to the fact that the ratio of non-severed type to severed type of β2-microglobulin increases with aging of epidermal keratinocytes. Accordingly, if the ratio of non-severed type to severed type of β2-microglobulin has decreased compared to the control in the skin cells and/or skin tissues contacted by the target substance, and the target substance can be evaluated to have the effect of decreasing the ratio of non-severed type to severed type of β2-microglobulin, then the target substance can be identified as being a substance effective in the prevention of skin aging.

EXAMPLES

The present invention is explained below in details using examples. It should be noted, however, that the present invention is not at all limited to these examples.

Example 1

Method of Experiment

1. Cell Culture

Using a medium KGM (+) prepared by adding additive factors (0.1 ng/ml EGF, 0.03 mg/ml bovine pituitary medium, 5 μg/ml insulin, 0.5 μg/ml hydrocortisone, GA-1000) to a serum-free basal medium (KBM, Cambrex Corporation), normal human epidermal keratinocytes (NHEK, Cambrex Corporation) were cultured in a 37° C., 5% $CO_2$ incubator. To collect the supernatant of culture (CM; Conditioned Medium) and cell extracts (CL: Cell Lysates), cells were inoculated in $5\times10^5$-cells/150-mm dishes and the medium was changed every two days to continue culturing until saturation. For passage of culture, cells were inoculated in $1\times10^5$-cells/60-mm dishes and the medium was changed every two days to continue culturing until reaching 80% saturation, upon which the culture was passed. NHEK could be cultured successively for five passages or so, and fifth-passage cells were used as aged cells in this experiment.

2. Measurement of SA-β-Gal in Each Passage of Normal Human Epidermal Keratinocytes (NHEK)

SA-β-Gal in each passage of NHEK was measured using a senescent cells staining kit (Sigma Corporation). Separately from those used for passage, cells were inoculated in three $1\times10^5$-cells/60-mm dishes and when 80% saturation was reached, the cells were fixed for 7 minutes at room temperature in an aqueous solution containing 2% formaldehyde and 0.2% glutaraldehyde. Furthermore, the cells were washed three times using 1×PBS (−), after which a staining solution was added to stain the cells overnight at 37° C. The number of SA-β-Gal stained cells per 100 cells was measured for each of the three dishes.

3. Preparation of CM and CL 3-1. Preparation of CM

A dish containing saturated NHEK was washed twice using KBM and cultured for one day after changing the medium to KBM to completely remove the additive factors. Two days after changing the medium to KBM, CM was collected. The collected CM was centrifuged for 10 minutes at 130×g to remove suspended cells, and then centrifuged again for 30 minutes at 10,000×g, after which supernatant was collected. Ammonium sulfate (Wako Pure Chemical Industries, Ltd.) was added to this CM to achieve 80% saturation and the mixture was agitated to fully dissolve solids, and the obtained liquid was let stand overnight at 4° C. Thereafter, the liquid was centrifuged for 30 minutes at 25,000×g to precipitate protein, and the precipitate was dissolved in 20 mM Tris-HCl (pH 7.4) until a concentration of 500 times to condense the CM. Furthermore, the condensed CM was dialyzed using 20 mM Tris-HCl (pH 7.4).

A fixed quantity of protein was measured by the Bradford method using a DC protein assay kit (Bio-Rad Laboratories Inc.) and used as a Western blotting sample. For two-dimensional electrophoresis, the prepared CM was freeze-dried and the obtained dry powder was dissolved in a two-dimensional electrophoresis sample preparation (6.5M urea (ICN Biomedicals, Inc.), 1.5M thiourea (Sigma Corporation), 0.15% SDS (Wako Pure Chemical Industries, Ltd.), 0.85% Triton X-100 (Wako Pure Chemical Industries, Ltd.), 0.4% CHAPS (Dojindo Laboratories), 2.5 mM tributyl phosphine (Wako Pure Chemical Industries, Ltd.)) to achieve the final concentration of 500 times, and a fixed quantity of protein was measured by the dot blotting method.

3-2. Preparation of CL

The dish from which the CM had been collected was washed three times using PBS (−), and then frozen at −30° C. to destroy the cell membrane. Thereafter, cells were collected using a cell scraper (Sumitomo Bakelite Co., Ltd.) and given ultrasonic treatment for 30 seconds. The obtained cells were mixed with 1% Triton X-100 and let stand for 30 minutes at 4° C. Next, the cells were centrifuged for 30 minutes at 15,000×g to remove insolubles, and supernatant was taken as a sample.

A fixed quantity of protein was measured using the dot blotting method to use as a Western blotting sample.

4. Two-Dimensional Electrophoresis (2-DE) Analysis of Protein 4-1. First-Dimension Isoelectric Focusing Electrophoresis 60 μg of protein was mixed in a gel-swelling solution (5M urea (Wako Pure Chemical Industries, Ltd.), 2M thiourea (Wako Pure Chemical Industries, Ltd.), 0.5% ampholytes (pH 3.5 to 10) (Amersham Biosciences), 0.0025% orange G (Wako Pure Chemical Industries, Ltd.), 2.5 mM tributyl phosphine (Wako Pure Chemical Industries, Ltd.), 1% Triton X-100) so that the total quantity becomes 340 μl, after which the mixture was added to an Immobiline DryStrip gel (18 cm, pH 3 to 10, NL) (Amersham Biosciences) to swell overnight at 20° C. Using an electrophoresis system (Anatech Corporation), in the first-dimension isoelectric focusing electrophoresis was performed at 20° C. using a program specifying 2 hours at 500 V, 1 hour at 700 V, 1 hour at 1000 V, 1 hour at 1500 V, 1 hour at 2000 V, 1 hour at 3000 V, and 10 hours at 3500 V. After the electrophoresis, the gel was soaked in a SDS equalizing buffer (5.8 M urea, 0.06M thiourea, 0.5% dithiothereitol (DTT, Wako Pure Chemical Industries, Ltd.), 25% glycerol (Wako Pure Chemical Industries, Ltd.), 0.0025% BPB (Wako Pure Chemical Industries, Ltd.)) and equalized for 1 hour at room temperature.

4-2. Second-Dimension SDS-PAGE

In the second dimension, SDS-PAGE was performed using a Tris-Tricine buffer (cathode buffer: 0.05M Tris, 0.05M Tricine (Bio-Rad Laboratories Inc.), 0.05% SDS; anode buffer: 1M Tris-HCl (pH 8.8)) and 7.5% acrylamide gel of 18 cm×18 cm.

4-3. Electrophoresis Blotting Method

The gel completing SDS-PAGE was transferred for 2 hours to PVDF membranes of 20 cm×20 cm (ProBlot Membranes (Applied Biosystems)) using a semi-dry type transfer system (Nihon Eido Co., Ltd.) at a constant current of 150 mA. For the transfer buffer, anode liquid 1 comprising 0.3M Tris-HCl (pH 10.4) and 20% methanol (Wako Pure Chemical Industries, Ltd.), anode liquid 2 comprising 25 mM Tris-HCL (pH 10.4) and 20% methanol, and cathode liquid comprising 25 mM Tris-HCl (pH 10.4), 20% methanol and 40 mM 6-amino hexanoic acid (Wako Pure Chemical Industries, Ltd.) were used. The transferred gel was washed three times for 20 minutes each using a TTBS buffer (20 mM Tris-HCl (pH 7.5) (Bio-Rad Laboratories Inc.), 500 mM NaCl (Wako Pure Chemical Industries, Ltd.), 0.3% Tween 20 (Bio-Rad Laboratories Inc.)), and then washed three times for 2 minutes each using pure water. Next, the PVDF membranes were sealed by vinyl membranes and soaked in a gold colloidal solution (Colloidal Gold Total Protein Staine (Bio-Rad Laboratories Inc.)), and the solution was shaken for 1 to 2 hours to stain the protein. Thereafter, the gold colloidal solution was removed and the residue was washed five times for 1 minute each using pure water and then dried.

5. Identification of Protein 5-1. Reduced S-Alkylation and Protease Digestion of Protein Transferred to PVDF Membranes Spots were cut off from the protein transferred to PVDF membranes and placed in a tube, to which 100 to 300 μl of a reducing buffer (8M guanidine-HCl (pH 8.5), (Wako Pure Chemical Industries, Ltd.), 0.5M Trisbase (Wako Pure Chemical Industries, Ltd.), 0.3% EDTA-2Na (Wako Pure Chemical Industries, Ltd.), 5% acetonitrile (Wako Pure Chemical Industries, Ltd.)) was added. Next, 1 mg of DTT dissolved in reducing buffer was added to replace the interior of the tube with nitrogen gas, after which the tube was left stationary at room temperature for 1 hour to reduce the protein. Thereafter, 3 mg of a monoiodoacetic acid (Wako Pure Chemical Industries, Ltd.) dissolved in 1M NaCl (Wako Pure Chemical Industries, Ltd.) was added and the mixture was agitated for 15 to 20 minutes by blocking light to achieve S-carboxymethylation. The PVDF membranes were then removed and washed for 5 minutes using pure water under agitation, after which the membranes were agitated in a similar manner in 2% acetonitrile (Wako Pure Chemical Industries, Ltd.). The PVDF membranes were then removed and transferred into a tube containing a Lys-C digesting buffer (70% acetonitrile/20 mM Tris-HCl (pH 9.0)) and rinsed two to three times, followed by soaking in the Lys-C digesting buffer to implement protease digestion for 1 hour.

5-2. Mass Spectrometry and Peptide Mass Finger Printing

The protease-digested solution was diluted seven times using distilled water to an acetonitrile concentration of 10%. As a pretreatment, suction and discharge was repeated several times using 50% acetonitrile/0.1% trifluoro-acetic acid (TFA, Wako Pure Chemical Industries, Ltd.), and several times using 2% acetonitrile/0.1% TFA, in order to activate the filler part of the ZipTipc18 pipette tip (Millipore Corporation). Next, a protease-digested solution was suctioned and discharged several times using the activated ZipTipc18 pipette tip to cause the fragmented peptide to be adsorbed to the filler part. Furthermore, 2% acetonitrile/0.1% TFA was suctioned and discharged several times to remove salts. Next, 0.5 to 1.0 µl of a saturated matrix solution dissolved in 50% acetonitrile/0.1% TFA was suctioned, and after 10 seconds the suctioned solution was dripped onto the target probe supplied with the mass spectrometer. The sample was dried and solidified, and then measured with the mass spectrometer (MALDI-TOF MS). Based on the obtained value of mass, the protein was identified using a database (MS-Fit, Mascot Search).

6. Western Blotting Method

SDS-PAGE was performed with a Laemmli Tris-Glycin system using a Western blotting sample. After the SDS-PAGE, protein in the gel was transferred to PVDF membranes (Millipore Corporation) at a constant current of 0.8 mA per 1 cm$^2$, and then soaked in 5% skim milk/PBS (−) and blocked overnight at 4° C. The PVDF membranes were washed three times using 0.1% Tween 20/PBS (−), and then soaked in each primary antibody solution and shaken for 1 hour at room temperature.

The types of primary antibodies used, and their dilution factors, are as follows: rabbit anti-maspin polyclonal antibody (Santa Cruz Biotechnology) (diluted by 1000 times), mouse anti-cystatin A monoclonal antibody (Sigma) (diluted by 1000 times), rabbit anti-kallikrein 7 polyclonal antibody (Santa Cruz Biotechnology) (diluted by 1000 times), sheep anti-PAI-1 polyclonal antibody (Biopool) (diluted by 1000 times), mouse anti-PAI-2 monoclonal antibody (American Diagnostica) (diluted by 1000 times), rabbit anti-uPA polyclonal antibody (Santa Cruz Biotechnology) (diluted by 1000 times), rabbit anti-matriptase polyclonal antibody (Calbiochem) (diluted by 1000 times), rat anti-GRP 94 monoclonal antibody (Stressgeen) (diluted by 1000 times), mouse anti-HSP 70 monoclonal antibody (Santa Cruz Biotechnology) (diluted by 1000 times), mouse anti-HSP 90 monoclonal antibody (Santa Cruz Biotechnology) (diluted by 1000 times), rabbit anti-enolase-1 polyclonal antibody (Santa Cruz Biotechnology) (diluted by 1000 times), rabbit anti-annexin II polyclonal antibody (Santa Cruz Biotechnology) (diluted by 1000 times), rabbit anti-ezrin/radixin/moesin polyclonal antibody (Chemicon) (diluted by 1000 times), mouse anti-gelsolin monoclonal antibody (Sigma Corporation) (diluted by 1000 times), mouse anti-galectin-1 monoclonal antibody (R&D Systems) (diluted by 1000 times), mouse anti-galectin-3 monoclonal antibody (Novocastra Laboratories) (diluted by 1000 times), mouse anti-galectin-7 monoclonal antibody (R&D Systems) (diluted by 1000 times), goat anti-IGFBP-3 polyclonal antibody (Santa Cruz Biotechnology) (diluted by 1000 times), rabbit anti-matriptase polyclonal antibody (Calbiochem) (diluted by 1000 times), mouse anti-β2-microglobulin monoclonal antibody (Sigma) (diluted by 1000 times), mouse anti-keratin 3 monoclonal antibody (Cymbus Biotechnology) (diluted by 1000 times), mouse anti-keratin 5 monoclonal antibody (Chemicon International Inc.) (diluted by 1000 times), mouse anti-keratin 7 monoclonal antibody (Chemicon) (diluted by 1000 times), mouse anti-keratin 8 monoclonal antibody (Chemicon) (diluted by 1000 times), mouse anti-keratin 10 monoclonal antibody (Chemicon) (diluted by 1000 times), mouse anti-keratin 13 monoclonal antibody (Cymbus Biotechnology) (diluted by 500 times), mouse anti-keratin 14 monoclonal antibody (Cymbus Biotechnology) (diluted by 500 times), mouse anti-keratin 15 monoclonal antibody (Cymbus Biotechnology) (diluted by 500 times), mouse anti-keratin 16 monoclonal antibody (Cymbus Biotechnology) (diluted by 500 times), mouse anti-keratin 17 monoclonal antibody (Chemicon) (diluted by 1000 times), mouse anti-keratin 18 monoclonal antibody (Chemicon) (diluted by 1000 times), mouse anti-keratin 19 monoclonal antibody (Cymbus Biotechnology) (diluted by 500 times), mouse anti-keratin 20 monoclonal antibody (Cymbus Biotechnology) (diluted by 500 times)

When sheep anti-PAI-1 polyclonal antibody, mouse anti-PAI-2 monoclonal antibody, rabbit anti-uPA polyclonal antibody or rabbit anti-matriptase polyclonal antibody was used as the primary antibody, biotinylated anti-goat IgG (Vector Laboratories) (diluted by 1000 times) or biotinylated anti-sheep IgG (Vector Laboratories) (diluted by 1000 times) was used as the secondary antibody. The sample was soaked in the secondary antibody solution and shaken for 1 hour at room temperature. Next, the sample was soaked in a solution of alkaline phosphatase-conjugated avidin D (Vector Laboratories) (diluted by 1000 times) and reacted for 1 hour at room temperature. Next, 0.6 mg/ml 5-bromo-4-chloro-3-indolylphosphate (Vector Laboratories), 1.2 mg/ml nitroblue-tetrazolium (Vector Laboratories), 0.1M Tris-HCl (pH 9.5) and 5 mM $MgCl_2$ (Wako Chemicals, Japan) were used to develop color.

When a primary antibody not specified above was used, horseradish peroxidase labeled anti-mouse IgG (Amersham Bioscience) (diluted by 5000 times), horseradish peroxidase labeled anti-rabbit IgG (Amersham Bioscience) (diluted by 5000 times), horseradish peroxidase labeled anti-rat IgG (Amersham Bioscience) (diluted by 5000 times) or horseradish peroxidase labeled anti-goat IgG (Santa Cruz) (diluted by 5000 times) was used as the secondary antibody. Next, an enhanced chemiluminescence (ECL) kit (Amersham Bioscience) was used to implement detection.

7. Judgment as a Skin Aging Marker

The amount of expression of protein detected by the Western blotting method was quantified using NIH image and the amount of expression of fifth-passage protein was divided by the amount of expression of second-passage protein. If the calculated value was 2.0 or more, it was determined that the amount of expression increased significantly with aging of epidermal keratinocytes. If the calculated value was less than 0.5, it was determined that the amount of expression decreased significantly with aging of epidermal keratinocytes. If the calculated value was 0.5 or more but less than 2.0, on the other hand, it was determined that expression did not change with aging of epidermal keratinocytes.

Result of Experiment
1. Change in Form with Aging of Epidermal Keratinocytes

Normal human cells stop proliferating after splitting a specified number of times. This phenomenon is called "cell aging" and the splitting limit varies depending on the type of cell. Human epidermal keratinocytes used in this experiment stop proliferating roughly after five passages through repeated passages of culture. FIG. 1 (a) plots the number of days before the 150-mm dish saturated for each passage. While it took six days for the dish to saturate with the first passage, the number of days increased to 28 with the fifth passage, suggesting an exponential increase in the proliferation rate from the first to fifth passages. Proliferation stopped completely with the sixth passage. In terms of cell form, fifth-passage cells were around twice as big as second-passage cells, and the former became flattened and enlarged reflecting the common trend observed in cell aging (FIG. 1 (b)).

Aging or terminal differentiation of cells is one cause of reduced proliferation of epidermal keratinocytes through repeated passages of culture. Accordingly, we examined the activity of SA-β-Gal identified as an aging marker for epidermal keratinocytes and skin tissues to determine if epidermal keratinocytes had actually aged, because this marker is known to express only when cells have aged, not when cells have terminally differentiated (Proc. Natl. Acad. Sci. USA, 92, 9363-9367, 1995). While second-passage cells were not stained blue to indicate SA-β-Gal, roughly a half of fifth-passage cells were stained blue (FIG. 2).

Based on the above result, we searched for cell aging markers by defining the second-passage cells as "young cells" and the fifth-passage cells as "aged cells."

Figure 3B:
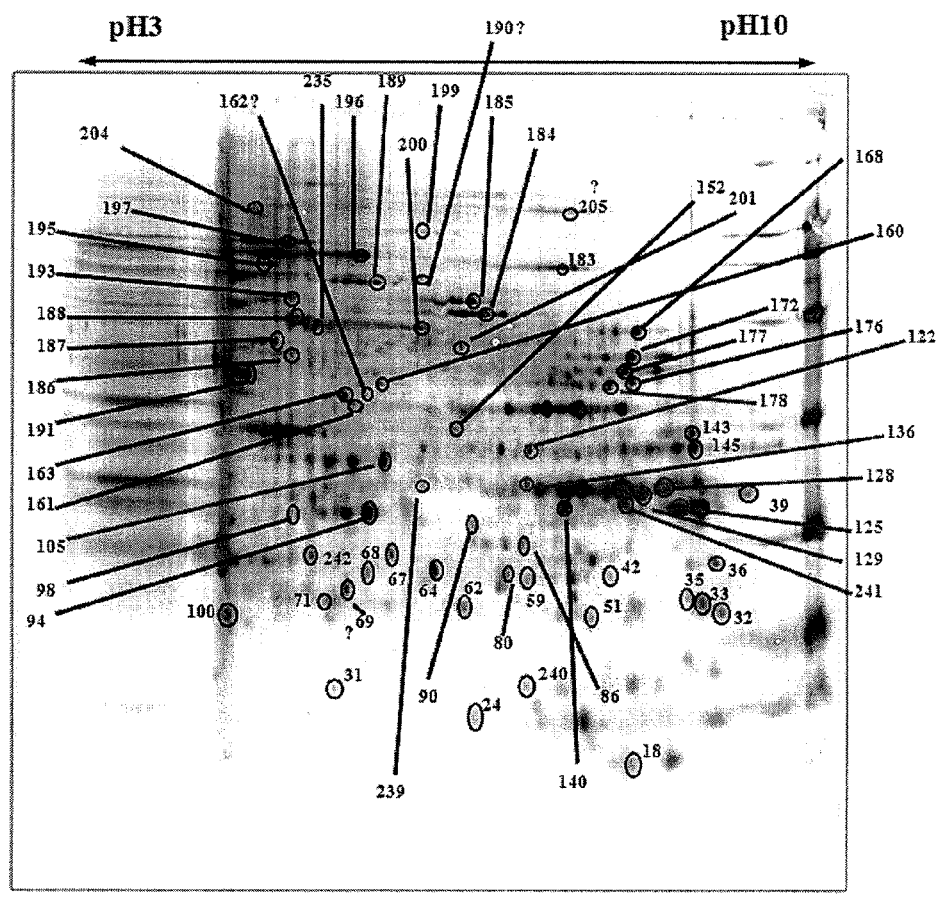

2. Analysis, by Two-Dimensional Electrophoresis, of Secretory Proteins that Change With Aging of Epidermal Keratinocytes CMs of second to fifth passages were prepared to analyze, by two-dimensional electrophoresis, those proteins whose expression changes (FIGS. 3(a) to 3(d)). When the spots taken from the supernatants of cell cultures of young cells (second passage, FIG. 3(a)) and aged cells (fifth passage, FIG. 3(b)) were compared, 19 proteins whose expression decreased with cell aging (Table 1) and 49 proteins whose expression increased with cell aging (Table 2) were identified. The identified proteins included known skin aging markers such as Maspin, Cystatin A and HSP 27, and therefore the analysis by two-dimensional electrophoresis performed in this test was deemed appropriate in identifying proteins that change with aging of skin. Since this test used a technology that makes identification of ultratrace proteins (1 femto-mol or less) possible, new skin aging marker proteins were also identified in addition to the known skin aging marker proteins. The identified key secretory proteins whose expression decreased with aging of epidermal keratinocytes included β2-microglobulin, PAI-1 and Kallikrein 7, among others. On the other hand, the identified secretory proteins whose expression increased with aging of epidermal keratinocytes included Moesin, Keratin 1 and Keratin 9, among others.

Table 1 lists the proteins whose expression decreased with aging of epidermal keratinocytes in the two-dimensional electrophoresis analysis.

TABLE 1

| Spot number | WM(kDa)/pI | Identified protein | |
|---|---|---|---|
| 7 | 15/8.0 | Pregnancy-specific beta-1 glycoprotein 2 | |
| 9 | 13/8.2 | Profilin | * |
| 12, 22, 221 | 18/7.2 | Cystatin M | |
| 21, 23, 219, 220, 222 | 12/7.2 | β-2 microglobulin | * |
| 206, 207 | 45/7.2 | Plasminogen activator inhibitor-1 (PAI-1) | * |
| 208 | 41/7.5 | Enolase-1 | |
| 209 | 39/7.55 | Asparate transaminase | * |
| 210, 211 | 41/7.2 | Squamous cell carcinoma antigen 1 (SCCA 1) | |
| 212 | 30/6.7 | Phospoglycerate mutase 1 | |
| 213 | 28/8.8 | Paroxiredotoxin 8 | * |
| 214 | 29/6.6 | Isopentenyl-diphosphate-isomerase 1 (IPP 1) | * |
| 217 | 28/5.4 | ER-localized type1 transmembrane adaptor precursor | * |
| 218 | 25/5.1 | Glutathione S-transferace | |
| 223 | 33/8.0 | Integrin-linked kinase (ILK) | * |
| 226 | 31/7.8 | Stratum corneum chymotryptic enzyme protein (Kallkrein 7) | * |
| 227 | 30/4.8 | Rho GDP dissociation inhibitor (Rho-GDI) | |
| 228 | 14/7.9 | Thrombospondin 1 | * |
| 229 | 14/5.2 | T cell antigen receptor a | * |
| 230 | 12/5.0 | Cystatin 8 | |

* New protein identified by this test as an aging marker for epidermal keratinocytes Table 2 lists the proteins whose expression increased with aging of epidermal keratinocytes in the two-dimensional electrophoresis analysis.

TABLE 2

| Spot number | Mr kDa/pI | Identified protein | |
|---|---|---|---|
| 18 | 10/7.4 | Phosphoglycerate mutase 1 | |
| 24 | 13/5.7 | Fatty acid binding protein 5 (FABP 5) | |
| 31 | 14/4.1 | Actin related protein 2/3 complex subunit 5 | * |
| 32 | 23/8.6 | Proteasome subunit b5 | * |
| 33 | 24/8.4 | Peroxiredoxin 1 | * |
| 35 | 24/8.4 | Proteasome subunit b1 | * |
| 36 | 29/8.6 | Proteasome subunit a7 | * |
| 39 | 36/9.0 | Mitochondrial maltate dehydrogenase | * |

TABLE 2-continued

| Spot number | Mr kDa/pI | Identified protein | |
|---|---|---|---|
| 42, 59 | 26/7.3 | Triosephosphate isomerase (Tin) | |
| 51 | 22/7.1 | Manganese superoxide dismutase | |
| 62 | 23/5.6 | Proteasome subunit b3 | * |
| 64, 68 | 26/5.3 | Heat shock protein 27 kDa (HSP 27) | |
| 67 | 29/4.8 | Proteasome subunit b7 | * |
| 80 | 26/6.1 | Proteasome subunit a6 | * |
| 86 | 30/6.3 | Purine nucleoside phosphorylase | |
| 90 | 32/5.7 | Delta3,5-delta2,4-dienoyl-CoA isomerase | * |
| 94 | 34/4.5 | L-lactate dehydrogenase B | * |
| 100 | 20/3.0 | Similar to tubulin b5 | * |
| 105 | 40/4.8 | Maspin | |
| 125, 128, 129, 241 | 34/8.2 | Annexin A2 | |
| 136 | 38/6.3 | Annexin 1 | |
| 140 | 34/6.8 | Cytosolic malate dehydrogenase | * |
| 143 | 44/8.3 | Phospholycerate kinase 1 | |
| 145 | 41/8.3 | Fructose-bisphosphate aldolase A | * |
| 152 | 45/5.6 | Adenosyl homocysteinase | * |
| 160 | 53/4.8 | Cytosolic nonspecific dipeptidase | * |
| 161 | 48/4.3 | Actin-related protein 3 | * |
| 163 | 50/4.2 | Glutathione synthetase | * |
| 168 | 65/7.6 | Transketolase | * |
| 172 | 59/7.5 | Pyruvate kinase M1 isozyme | * |
| 176, 178 | 54/7.6 | UTP-glucose-1-phosphate uridyl transferase 2 | * |
| 177 | 58/7.4 | Adanylyl cyclase-associated protein 1 (CAP 1) | * |
| 183 | 96/6.8 | Elongation factor 2 | * |
| 184 | 72/5.9 | Moesin | * |
| 185 | 76/5.8 | Ezrin | |
| 186 | 60/3.6 | Ubiquitin carboxyl-terminal hydrolase 14 | * |
| 187 | 62/3.4 | Keratin 2 | * |
| 188, 235 | 70/3.6 | Heat shock 70 kDa protein (HSP 70) | |
| 189 | 85/4.8 | Gelsolin | |
| 191 | 55/3.1 | Tubulin a6 | |
| 193 | 77/3.6 | Acylamino-acid-releasing enzyme | * |
| 195 | 95/3.4 | Transitional endoplasmic reticulum ATPase | * |
| 196 | 100/4.5 | Actinin, a1 | * |
| 197 | 110/3.6 | Major vault protein | * |
| 198 | 115/4.2 | Vinculin isoform VCL | * |
| 200, 201 | 66/5.2 | Keratin 1 | * |
| 204 | 150/3.3 | Leukotriene A4 hydrolase | * |
| 239 | 37/5.2 | 60S acidic ribosomal protein P0 | * |
| 242 | 29/3.8 | Caspase 14 | * |

* New protein identified by this test as an aging marker for epidermal keratinocytes 3. Analysis, by Western Blotting, of Secretory Proteins and Intracellular Proteins whose Expression Changes with Aging of Epidermal Keratinocytes To further confirm the aforementioned changes in protein expressions with aging, Western blotting was performed using antibodies for respective proteins. In the analysis by two-dimensional electrophoresis, all proteins were taken by the same mass to implement comparative analysis. It should be noted, however, that epidermal keratinocytes change their form and become flattened and enlarged as they age, and thus the cell count will vary even when the saturation condition is kept the same. When the mass of secretory protein per cell was actually calculated, the protein mass increased with aging of epidermal keratinocytes in all samples including those of supernatant of cell culture (CM), cell liquid (CL) and extracellular matrix (ECM). Accordingly, Western blotting was used to examine the change in the amount of expression of each protein for two groups of samples: one consisting of samples having the same number of cells and the other consisting of samples having the same protein mass. To verify which of these two sample groups was more suited for examination of aging of epidermal keratinocytes, how expression would change was examined for Laminin 5 (trimer of Laminin α3, Laminin β3 and Laminin γ2) which is a key component of the basal skin membrane in which damage builds up as the skin ages and which is also an important factor in basal membrane care (J. Soc. Cosmet. Chem. Jpn., Sosetsu (Overview), 35 (1), 1-7, 2001), and also for Fibronectin whose expression is known to drop with aging of skin (Ann Pathol., 4 (3), 185-94, 1984). As a result, although the expression of Laminin 5 in CM did not change in the samples having the same number of cells, the amount of expression decreased in the samples having the same protein mass (FIG. 4). Similarly, the expression of Fibronectin in CM increased in the samples having the same number of cells, while the amount of expression decreased in the samples having the same protein mass. The above results show that it is more appropriate to analyze change in expression using samples having the same protein mass.

Here, the results of Western blotting using various antibodies are shown in both conditions; i.e., by aligning the number of cells and protein mass. From the aforementioned conclusion, however, the results of samples having the same protein mass were used to determine presence/absence of correlation with aging of epidermal keratinocytes.

First with proteases and protease inhibitors, serine protease inhibitors Maspin and PAI-2 and cysteine protease inhibitor Cystatin A all exhibited an increased amount of expression with aging (FIG. 5 (a)(b)). On the other hand, serine proteases Kallikrein 7 and uPA, membrane-binding serine protease Matriptase and serine protease inhibitor PAI-1 all exhibited a decreased amount of expression with aging. While β2-microglobulin is known to be severed by acid proteases, it was found that the ratio of severed type (13 kDa) would decrease and that of non-severed type (14 kDa) would increase with aging (FIG. 5 (a)).

HSP 70, HSP 90 and GRP 94 (only GRP 94 has a signal peptide), which are all an intracellular protein and a type of heat shock protein, were secreted more in CM with aging. However, the amount of expression in CL did not change with any of them (FIG. 6).

Enolase-1 which is an intracellular glycolysis enzyme, Annexin II that bonds with phospholipids in cell membrane, and cytoskeletal proteins Ezrin, Moesin and Radixin were found to secrete more in CM with aging (FIG. 7). Gelsolin, which is a cytoskeletal protein, did not change the amount of secretion in CM, but its amount of expression in CL increased (FIG. 7).

Galectin-1, Galectin-3 and Galectin-7 of the lectin family, and IGFBP-3 showed a significant increase in the amount of expression of the protein secreted extracellularly with aging of epidermal keratinocytes (FIG. 8). On the other hand, Galectin-1, Galectin-3, Galectin-7 and IGFBP-3 were not detected in CL (FIG. 8).

Among the various types of Keratins that are cytoskeletal proteins, 13 types (Keratin 3, 5, 7, 8, 10, 13, 14, 15, 16, 17, 18, 19 and 20) were examined. As a result, Keratin 10, 13, 14, 15, 16, 18, 19 and 20 showed a significant increase in their expression in cells with aging of epidermal keratinocytes (FIG. 9). On the other hand, the expression of Keratin 7 in cells decreased significantly with aging of epidermal keratinocytes (FIG. 9). No change in expression was observed for Keratin 3, 5, 8 and 17. Keratins were not detected in CM.

Table 3 lists the proteins whose expression changed with aging of epidermal keratinocytes in the one-dimensional Western blotting analysis.

Table 3 lists the proteins whose expression changed with aging of epidermal keratinocytes in the one-dimensional Western blotting analysis.

TABLE 3

| Protein category | Protein name | change in expression: (passage 5/passage 2) | |
|---|---|---|---|
| | | CM | CL |
| Protease, protease inhibitor | kallikrein 7 | ↓ (0.1) | ND |
| | PAI-1 | ↓ (0.1) | ND |
| | uPA | ↓ (0.1) | ↓ (0.3) |
| | matriptase | ↓ (0.4) | ↓ (0.2) |
| HSP | GRP94 | ↑ (22.0) | → |
| | HSP70 | ↑ (12.4) | → |
| | HSP90 | ↑ (19.2) | → |
| Galectin | galectin-1 | ↑ (20.0) | ND |
| | galectin-3 | ↑ (2.2) | ND |
| | galectin-7 | ↑ (7.9) | ND |
| | IGFBP-3 | ↑ (3.4) | ND |
| Cytoskeletal | enolase-1 | ↑ (6.1) | → |
| | annexin II | ↑ (12.6) | → |
| | ezrin/moesin/radixin | ↑ (10.6) | → |
| | gelsolin | → | ↑ (2.3) |
| Keratin | keratin 3 | ND | → |
| | keratin 5 | ND | → |
| | keratin 7 | ND | ↓ (0.2) |
| | keratin 8 | ND | → |
| | keratin 10 | ND | ↑ (4.0) |
| | keratin 13 | ND | ↑ (3.1) |
| | keratin 14 | ND | ↑ (2.4) |
| | keratin 15 | ND | ↑ (5.0) |
| | keratin 16 | ND | ↑ (2.4) |
| | keratin 17 | ND | → |
| | keratin 18 | ND | ↑ (3.1) |
| | keratin 19 | ND | ↑ (2.0) |
| | keratin 20 | ND | ↑ (2.2) |
| Other | β2-microglobulin | ↑ [*] | ↑ (3.5) |

↑: Expression increased
↓: Expression decreased
→: No change in expression
ND: Not detected
CM: Supernatant of culture
CL: Cell extract
[*]: Ratio of non-severed type to severed type increased Example 2

Method of Experiment

1. Measurement of Elasticity and Volumetric Ratio of Lines at Corner of Eye

Elasticity and volumetric ratio of lines were measured at the corner of the eye on 59 women in their 20s to 60s. Elasticity at the corner of the eye was measured as suction elasticity using a Cutometer (Courage+Khazaka electronic GmbH). Suction elasticity is a measure that provides an indicator of skin elasticity, and this elasticity has been shown to decrease with aging. Volumetric ratio of lines at the corner of the eye was measured via replica image analysis by collecting replicas from the corner of the eye using Skin Cast (Yamada Cosmetic Laboratories) which is a replica agent consisting of two parts. Replica image analysis was then performed using a reflective replica analysis system ASA-03RXD. The ASA-03RXD was used to irradiate parallel light onto the collected replica at an angle of 30 degrees and the obtained shadow image reflecting the shapes of lines was captured with a CCD camera and imported to a computer for image processing to measure the volumetric ratio of lines at the replica surface ($\mu m^3/mm^2/100$).

Volumetric ratio of lines has been shown to increase with aging.

2. Extraction of Proteins from Horny Cell Layer at Corner of Eye

The horny cell layer was peeled from the corner of the eye using a horny cell layer checker (Asahibiomed Co., Ltd.) on 59 women in their 20 to 60s, and protein was extracted from the obtained samples using a protein-extracting solution. To be specific, the horny cell layer checker was attached to the corner of the eye of the subject and the checker was gently rubbed from above with the fingertip. The sample collection was repeated three times, and then 50 μl of a protein-extracting solution (50 mM Tris-HCl (pH 7.5), 120 mM NaCl, 0.4% Igepal CA-630 (Sigma-Aldrich Co.)) was added to the horny cell layer attached to each of the three horny cell layer checkers and a cell scraper was used to spread the protein-extracting solution evenly over the horny cell layer, after which the solution was collected into a 1.5-ml plastic tube (Eppendorf AG).

The collected solution was centrifuged for 15 minutes at 10,000×g to precipitate insolubles, and supernatant was collected into a new 1.5-ml plastic tube. The mass of protein in the collected sample was measured using a DC assay kit.

3. Measurement of Skin Aging Markers

Using 10 μg of protein extracted from the horny cell layer at the corner of the eye, antibodies of Keratin 7, Keratin 15 and Kallikrein 7 stated in Example 1 were applied to implement detection by the Western blotting method. The intensity of detected bands was measured using a densitometer (Molecular Dynamics Co., Ltd.) and quantified using NIH image.

Result of Experiment

Among the proteins whose expression changes with aging of epidermal keratinocytes, Keratin 7, Keratin 10, Keratin 15 and Kallikrein 7 were examined to see if there was any correlation with the degree of aging of human skin.

Since Keratin 10 has been shown to decrease its expression with skin aging, which of Keratin 10, Keratin 7 and Keratin 15 would exhibit correlation with the degree of aging of human skin was examined. When the correlation of Keratin 10/Keratin 15 and age was examined, Keratin 10 showed no correlation with age, while Keratin 15 was correlated with age. Accordingly, it was found that Keratin 15 would provide a more appropriate skin aging marker than existing skin aging markers (FIGS. 10, 11).

As indicators of the degree of aging of human skin, elasticity and volumetric ratio of lines at the corner of the eye were used as they have known correlation with age. On 59 women in their 20s to 60s who participated in the measurement of skin aging degree under this test, the elasticity at the corner of the eye decreased significantly with age, while the volumetric ratio of lines increased significantly (FIGS. 12, 13).

FIG. 14 shows the correlation between the amount of expression of Keratin 7 and the elasticity at the corner of the eye, while FIG. 15 shows the correlation between the amount of expression of Keratin 15 and the elasticity at the corner of the eye. The amount of expression of Keratin 7 decreased significantly as the elasticity at the corner of the eye dropped, while the amount of expression of Keratin 15 increased significantly as the elasticity at the corner of the eye dropped. FIG. 16 shows the correlation between the amount of expression of Keratin 7 and the volumetric ratio of lines, while FIG. 17 shows the correlation between the amount of expression of Keratin 15 and the volumetric ratio of lines. The amount of expression of Keratin 7 decreased significantly as the volumetric ratio of lines at the corner of the eye increased, while the amount of expression of Keratin 15 increased significantly as the volumetric ratio of lines at the corner of the eye increased.

The correlation of expression of Kallikrein 7 and degree of skin aging was also examined. FIG. 18 shows the correlation between the amount of expression of Kallikrein 7 and the elasticity at the corner of the eye, while FIG. 19 shows the correlation between the amount of expression of Kallikrein 7 and the volumetric ratio of lines at the corner of the eye. The amount of expression of Kallikrein 7 decreased significantly as the elasticity at the corner of the eye dropped, and also decreased significantly as the volumetric ratio of lines at the corner of the eye increased.

From the above results, three markers (Keratin 7, Keratin 10 and Kallikrein 7) identified using aging of epidermal keratinocytes as an indicator have a clear correlation with the degree of aging of human skin.

INDUSTRIAL FIELD OF APPLICATION

Proteins whose expression increases or decreases with aging of cells, as well as proteins that change from the severed type to non-severed type with aging of cells, were identified. These newly discovered proteins are expected to find use in counseling systems for cosmetics, etc., as a diagnostic marker for skin aging. Also, more effective cosmetics and health foods can be developed using the expressions of these proteins as indicators.

What is claimed is:

1. A method for determining the degree of skin aging, comprising: obtaining skin cells and/or skin tissues from a subject; and measuring production of preselected secretory proteins and/or intracellular proteins contained in the skin cells and/or skin tissues, thereby determining the degree of aging of the subject's skin, wherein the secretory proteins and/or intracellular proteins change their production with aging of skin, said secretory proteins and/or intracellular proteins being selected from the group consisting of Kallikrein 7, Glucose Regulated Protein (GRP) 94, Enolase-1, Radixin, Keratin 14, Keratin 20 and β2-microglobulin.

2. The method according to claim 1, wherein the production of the secretory proteins and/or intracellular proteins is measured at the protein level.

3. A method for identifying substances effective in inhibiting skin aging, comprising:
    (a) contacting a target substance with skin cells and/or skin tissues;
    (b) culturing for a specified time the skin cells and/or skin tissues in contact with the target substance in step (a);
    (c) measuring the production of the preselected secretory proteins and/or intracellular proteins contained in the skin cells and/or skin tissues cultured in step (b) according to the method of claim 1, wherein the secretory proteins and/or intracellular proteins change their production with aging of skin; and
    (d) evaluating the effect of the target substance on the production of the secretory proteins and/or intracellular proteins contained in skin cells and/or skin tissues, by comparing the production of the secretory proteins and/or intracellular proteins measured in step (c) against the production of the secretory proteins and/or intracellular proteins measured in step (c) using control skin cells and/or skin tissues wherein no target substance is used in step (a) and (b).

4. The method according to claim 1, wherein the secretory proteins and/or intracellular proteins is Kallikrein 7.

5. The method according to claim 1, wherein the production of preselected secretory proteins and/or intracellular proteins is measured per protein mass in the skin cells and/or skin tissues.

* * * * *

UNITED STATES PATENT AND TRADEMARK OFFICE
CERTIFICATE OF CORRECTION

PATENT NO. : 7,972,788 B2
APPLICATION NO. : 12/064602
DATED : July 5, 2011
INVENTOR(S) : Miyata et al.

It is certified that error appears in the above-identified patent and that said Letters Patent is hereby corrected as shown below:

On Title Page 1 (Item 56), Column 1, Line 2, under Other Publications, please change "senescene" to --senescence--.

On Title Page 1 (Item 56), Column 1, Line 24, under Other Publications, please change "Geromology:" to --Gerontology:--.

On Title Page 1 (Item 56), Column 1, Line 38, under Other Publications, please change "Managanese-" to --Manganese- --.

On Title Page 1 (Item 56), Column 1, Line 42, under Other Publications, please change "Sensescene,"" to --Senescence,"--.

On Title Page 1 (Item 56), Column 1, Line 45, under Other Publications, please change "Wwrner" to --Werner--.

On Title Page 2 (Item 56), Column 1, Line 24, under Other Publications, please change "Senescene" to --Senescence--.

On Title Page 2 (Item 56), Column 2, Line 9, under Other Publications, please change "Quatification" to --Quantification--.

On Title Page 2 (Item 56), Column 2, Line 13, under Other Publications, please change "Proteme" to --Proteome--.

On Sheet 5 of 23 (Fig. 3(c)), Line 9, please change "Peroxiredxin 1" to --Peroxiredoxin 1--.

On Sheet 5 of 23 (Fig. 3(c)), Line 12, please change "maltate" to --malate--.

On Sheet 5 of 23 (Fig. 3(c)), Line 18, please change "Glutathion" to --Glutathione--.

Signed and Sealed this
Tenth Day of April, 2012

David J. Kappos
*Director of the United States Patent and Trademark Office*

CERTIFICATE OF CORRECTION (continued)

U.S. Pat. No. 7,972,788 B2

On Sheet 5 of 23 (Fig. 3(c)), Line 29, please change "maltate" to --malate--.

On Sheet 5 of 23 (Fig. 3(c)), Line 30, please change "Phosphglycerate" to --Phosphoglycerate--.

On Sheet 6 of 23 (Fig. 3(d)), Line 12, please change "endplasmic" to --endoplasmic--.

On Sheet 6 of 23 (Fig. 3(d)), Line 20, please change "Asparatate" to --Aspartate--.

On Sheet 6 of 23 (Fig. 3(d)), Line 27, please change "Glutathion" to --Glutathione--.

In Column 2, Line 57, please change "femto-mol" to --femtomole--.

In Column 5, Line 49 (Approx.), after "eye" please insert --.--.

In Column 6, Line 13 (Approx.), please change "chymotrytic" to --chymotryptic--.

In Column 6, Line 58-89, please change "(Endoplasmin," to --(Endoplasmic,--.

In Column 8, Line 54, please change "Genlsolin" to --Gelsolin--.

In Column 16, Line 21-22, please change "dithiothereitol" to --dithiothreitol--.

In Column 17, Line 35, please change "Tris-Glycin" to --Tris-Glycine--.

In Column 17, Line 56, please change "(Stressgeen)" to --(Stressgen)--.

In Column 18, Line 28, after "times)" insert --.--.

In Column 20, Line 19 (Approx.), please change "femto-mol" to --femtomole--.

In Columns 19-20 (Table 1), Line 8, please change "Asparate" to --Aspartate--.

In Columns 19-20 (Table 1), Line 10, please change "Phospoglycerate" to --Phosphoglycerate--.

In Columns 19-20 (Table 1), Line 11, please change "Paroxiredotoxin" to --Peroxiredoxin--.

In Columns 19-20 (Table 1), Line 14, please change "S-transferace" to --S-transferase--.

In Columns 19-20 (Table 1), Line 16, please change "Kallkrein" to --Kallikrein--.

In Columns 19-20 (Table 2), Line 9, please change "maltate" to --malate--.

In Column 21 (Table 2), Line 16, please change "Pholycerate" to --Phosphoglycerate--.

CERTIFICATE OF CORRECTION (continued)
U.S. Pat. No. 7,972,788 B2

In Column 21 (Table 2), Line 25, please change "Adanylyl" to --Adenylyl--.

In Column 22, Line 61 (Approx.), please change "(FIG. 5(a)(b))." to --(FIGS. 5(a)(b)).--.

In Column 26, Line 23 (Approx.), in Claim 1, after "94," please insert --Galectin-1,--.